(12) United States Patent
Zheng et al.

(10) Patent No.: US 7,943,787 B2
(45) Date of Patent: May 17, 2011

(54) PREPARATION OF PENTAFLUOROSULFANYL (SF$_5$) HETEROCYCLES: PYRROLES AND THIOPHENES

(75) Inventors: Zhaoyun Zheng, Gainesville, FL (US); William R. Dolbier, Jr., Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 12/817,652

(22) Filed: Jun. 17, 2010

(65) Prior Publication Data

US 2011/0040103 A1 Feb. 17, 2011

Related U.S. Application Data

(60) Provisional application No. 61/187,909, filed on Jun. 17, 2009.

(51) Int. Cl.
- *C07D 207/18* (2006.01)
- *C07D 207/30* (2006.01)
- *C07D 333/06* (2006.01)
- *C07D 333/26* (2006.01)

(52) U.S. Cl. .......... 548/541; 548/560; 548/565; 549/62
(58) Field of Classification Search .......... None
See application file for complete search history.

(56) References Cited

U.S. PATENT DOCUMENTS 6,479,645 B1  11/2002  Lal et al.

FOREIGN PATENT DOCUMENTS

WO   WO-2007-106818   9/2007

OTHER PUBLICATIONS

Dolbier, Org. Lett., 8:5573 (2006).*
Dolbier, Jr., W.R. et al., "A convenient and efficient method for incorporation of pentafluorosulfanyl (SF$_5$) substituents into aliphatic compounds," *Journal of Fluorine Chemistry*, 2006, pp. 1302-1310, vol. 127.
Kellogg, R.M., "The molecules R$_2$CXCR$_2$ including Azomethine, Carbonyl and Thiocarbonyl Ylides. Their Synthesis, Properties and Reactions," *Tetrahedron*, 1976, pp. 2165-2184, vol. 32.
Nájera, C. et al., "Azomethine Ylides in Organic Synthesis," *Current Organic Chemistry*, 2003, pp. 1105-1150, vol. 7.
Ye, C. et al., "Synthesis of Pentafluorosulfanylpyrazole and Pentafluorosulfanyl-1,2,3-triazole and Their Derivatives as Energetic Materials by Click Chemistry," *Organic Letters*, 2007, pp. 3841-3844, vol. 9. No. 19.
La Porta, P. et al., "Synthesis of Methyl 3-Aryl-4-trifluoromethyl-1 H-pyrrole-2-carboxylates," *Synthesis*, Mar. 1994, pp. 287-290, vol. 3.

\* cited by examiner

*Primary Examiner* — Yong Chu
*Assistant Examiner* — Michael Barker
(74) *Attorney, Agent, or Firm* — Saliwanchik, Lloyd & Eisenschenk

(57) ABSTRACT

The subject invention pertains to pentafluorosulfonyl (SF5) substituted pyrroles, thiophenes, 3-pyrrolines and 2,5-dihydrothiophenes, as well as methods for their synthesis.

17 Claims, 27 Drawing Sheets

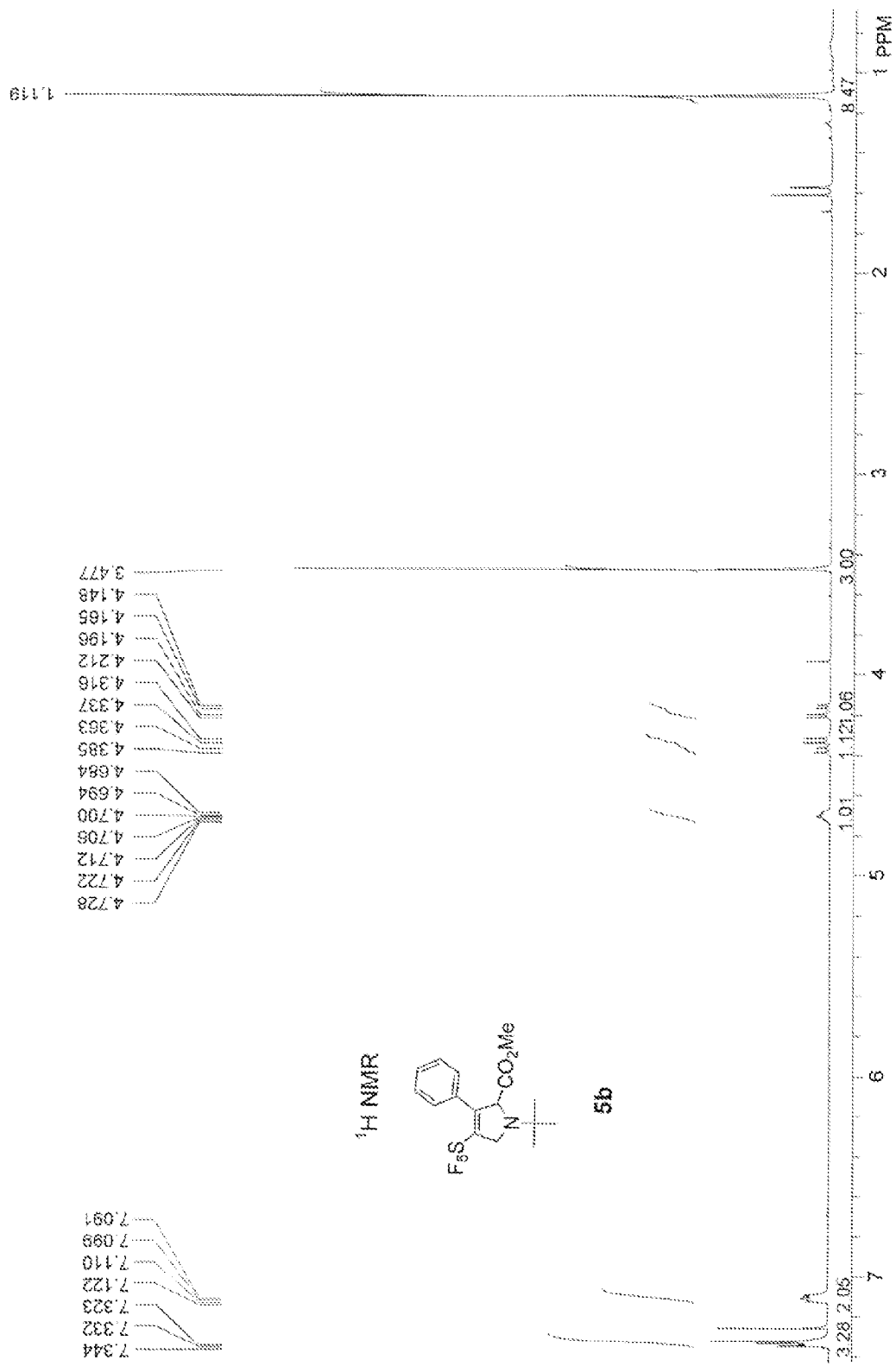

The regiochemistry was demonstrated by nOe's between 4.63 and 7.04

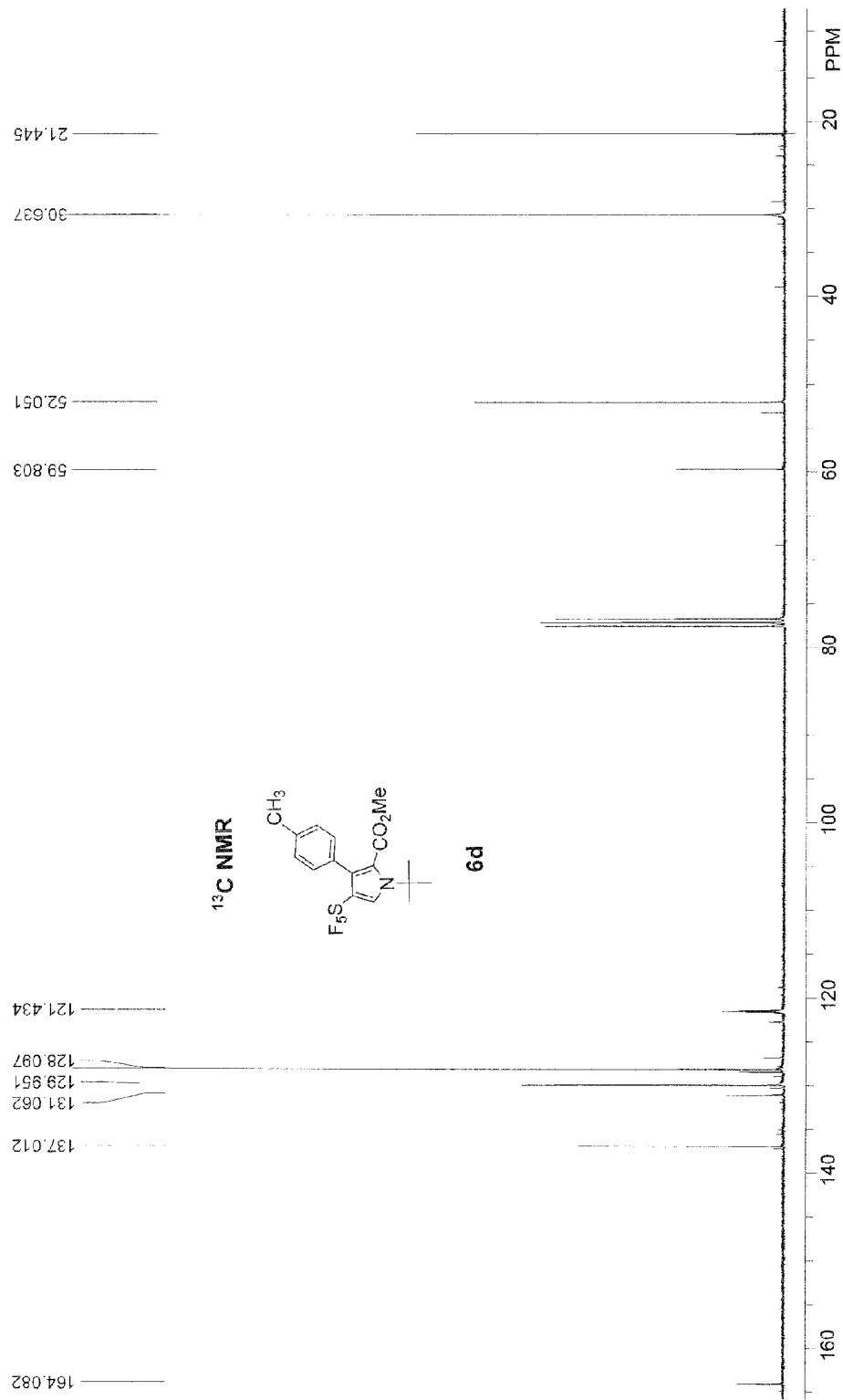

PREPARATION OF PENTAFLUOROSULFANYL (SF$_5$) HETEROCYCLES: PYRROLES AND THIOPHENES

CROSS REFERENCE TO RELATED APPLICATION

This application claims the benefit of U.S. Provisional Application Ser. No. 61/187,909, filed Jun. 17, 2009, the disclosure of which is hereby incorporated by reference in its entirety, including all figures, tables and amino acid or nucleic acid sequences.

BACKGROUND OF THE INVENTION

Only a few heterocycles bearing an SF$_5$-group have previously been known, including furans, for example Dolbier et al. *Org Lett* 8:5573-5575, and pyrazoles and triazoles, for example Ye et al. *Org Lett* 9:3841-3844. It is desirable to prepare other heterocycles bearing an SF$_5$-group for use as intermediates for the development of novel pharmaceutical, agricultural, or chemicals for other uses. Such heterocycles bearing an SF$_5$-group are also useful for other purposes, such as specialty fluids, ligands, and monomers to form polymers, for example to form conjugated polymers such as polythiophenes and polypyrroles. For these applications the increased density and/or the electron withdrawing properties imparted by the SF$_5$ group is exploited.

BRIEF SUMMARY OF THE INVENTION

Embodiments of the subject invention relates to novel pentafluorosulfanyl-containing heterocycles. Specifically, the subject invention relates to pentafluorosulfanyl-substituted heterocycles such as pyrroles, thiophenes, 3-pyrrolines and 2,5-dihydrothiophenes along with analogues of each of the aforementioned compounds. Exemplary compounds of the subject invention include, without limitation, 3-pentafluorosulfanyl-4-p-tolyl-dihydrothiophene (compound 1); 3-pentafluorosulfanyl-4-p-tolyl-thiophene (compound 2); methyl 1-tert-butyl-4-pentafluorosulfanyl-3-phenyl-2,5-dihydro-2H-pyrrole-2-carboxylate (compound 5b); methyl 1-tert-butyl-4-pentafluorosulfanyl-3-(2-phenylethyl)pyrrole-2-carboxylate (compound 6a); methyl tert-butyl-4-pentafluorosulfanyl-3-phenylpyrrole-2-carboxylate (compound 6b); methyl 1-tert-butyl-4-pentafluorosulfanyl-3-butylpyrrole-2-carboxylate (compound 6c); methyl 1-tert-butyl-4-pentafluorosulfanyl-3-p-tolylpyrrole-2-carboxylate (compound 6d); and methyl 4-pentafluorosulfanyl-3-(2-phenylethyl)pyrrole-2-carboxylate (compound 7). Other embodiments of the subject invention pertain to processes used to synthesize heterocycles substituted with a pentafluorosulfanyl group.

BRIEF DESCRIPTION OF THE DRAWINGS

FIGS. 1A-1C present NMR spectra for compound 4a. FIG. 1A is the $^1$H spectrum, FIG. 1B is the $^{13}$C spectrum, and FIG. 1C is the $^{19}$F spectrum.

FIG. 2A is the $^1$H spectrum, FIG. 2B is the $^{13}$C spectrum, and FIG. 2C is the $^{19}$F spectrum.

FIGS. 3A-3F present NMR spectra for compound 5b along with regiochemistry. FIG. 3A is the $^1$H spectrum, FIG. 3B is the $^{19}$F spectrum, and FIG. 3C illustrates results for nuclear Overhauser effect. FIGS. 3D, 3E, and 3F provide gradient-selected Heteronuclear Multiple Bond Coherence (gHMBC) spectra.

FIGS. 4A-4C present NMR spectra for compound 6a. FIG. 4A is the $^1$H spectrum, FIG. 4B is the $^{13}$C spectrum, and FIG. 4C is the $^{19}$F spectrum.

FIG. 5A is the $^1$H spectrum, FIG. 5B is the $^{13}$C spectrum, and FIG. 5C is the $^{19}$F spectrum.

FIG. 6A is the $^1$H spectrum, FIG. 6B is the $^{13}$C spectrum, and FIG. 6C is the $^{19}$F spectrum.

FIGS. 7A-7C present NMR spectra for compound 6d. FIG. 7A is the $^1$H spectrum, FIG. 7B is the $^{13}$C spectrum, and FIG. 7C is the $^{19}$F spectrum.

FIG. 5A is the $^1$H spectrum, FIG. 8B is the $^{13}$C spectrum, and FIG. 8C is the $^{19}$F spectrum.

DETAILED DISCLOSURE OF THE INVENTION

Figure 1A:
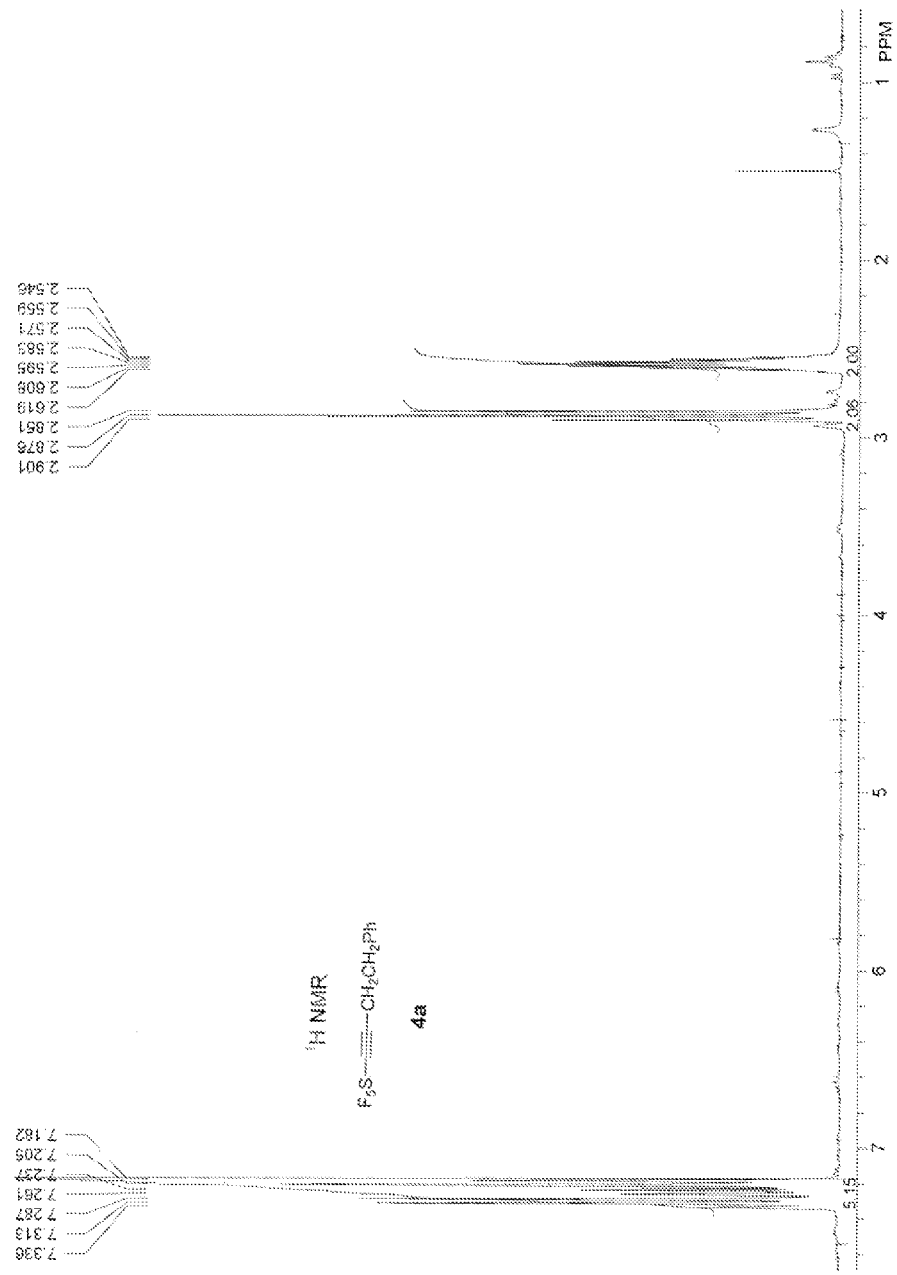
Figure 1B:
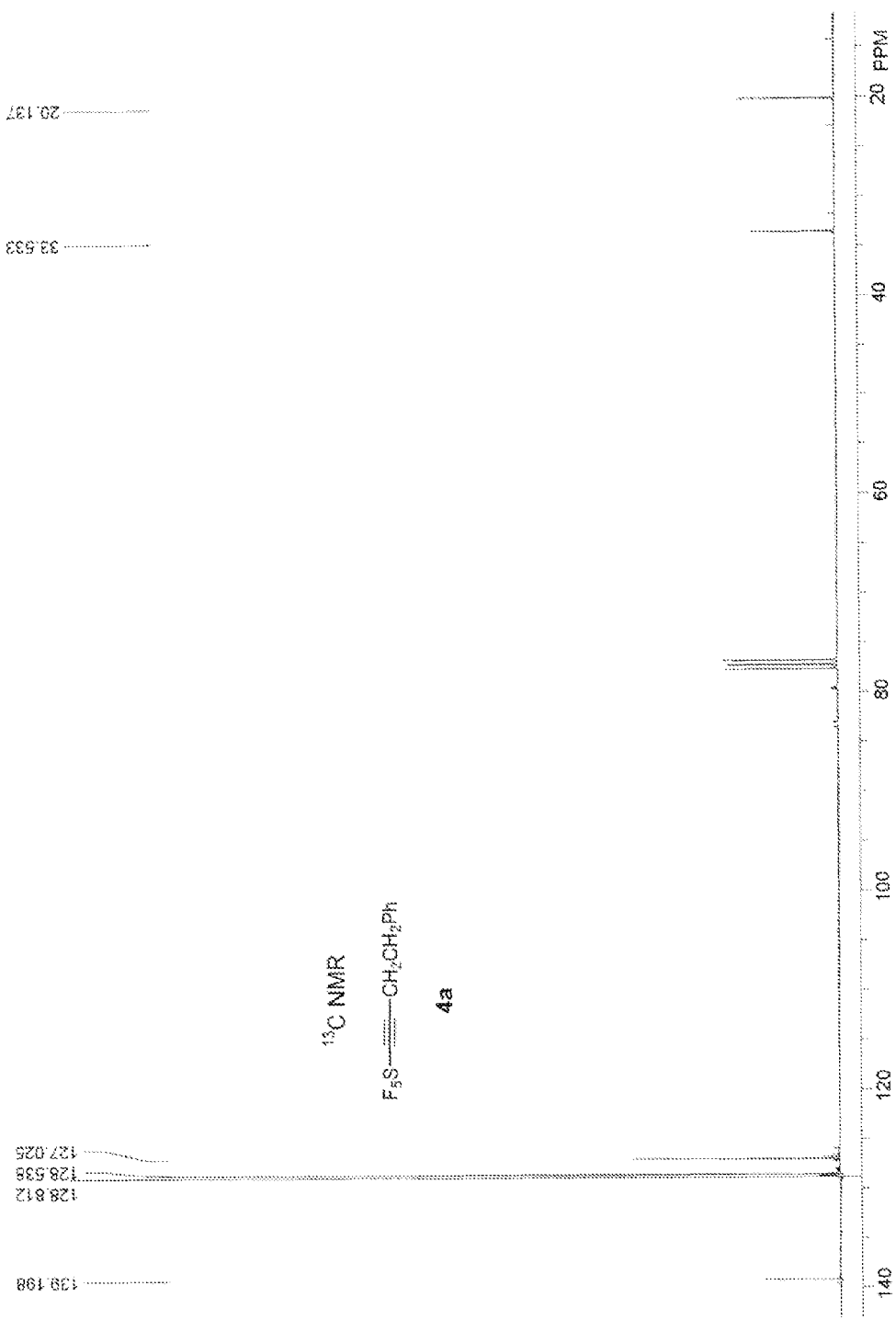
Figure 1C:
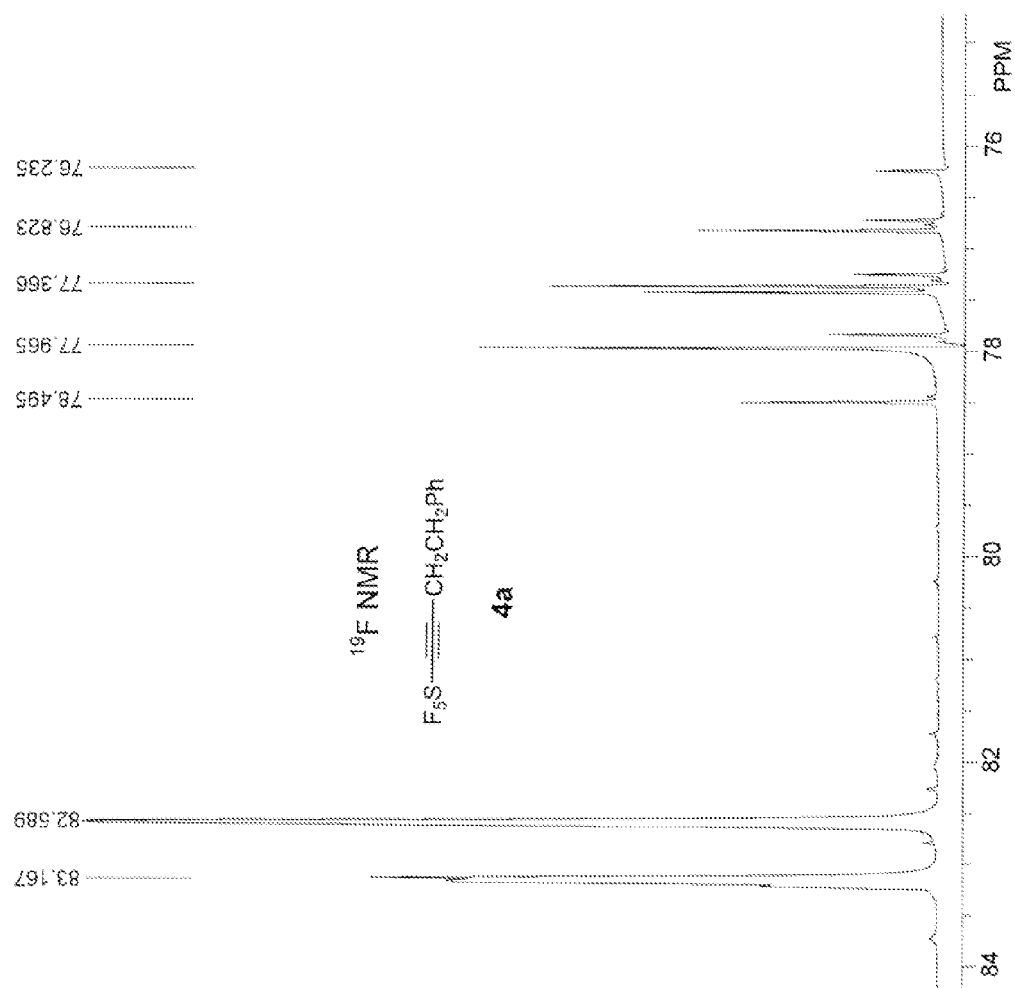
Figure 2A:
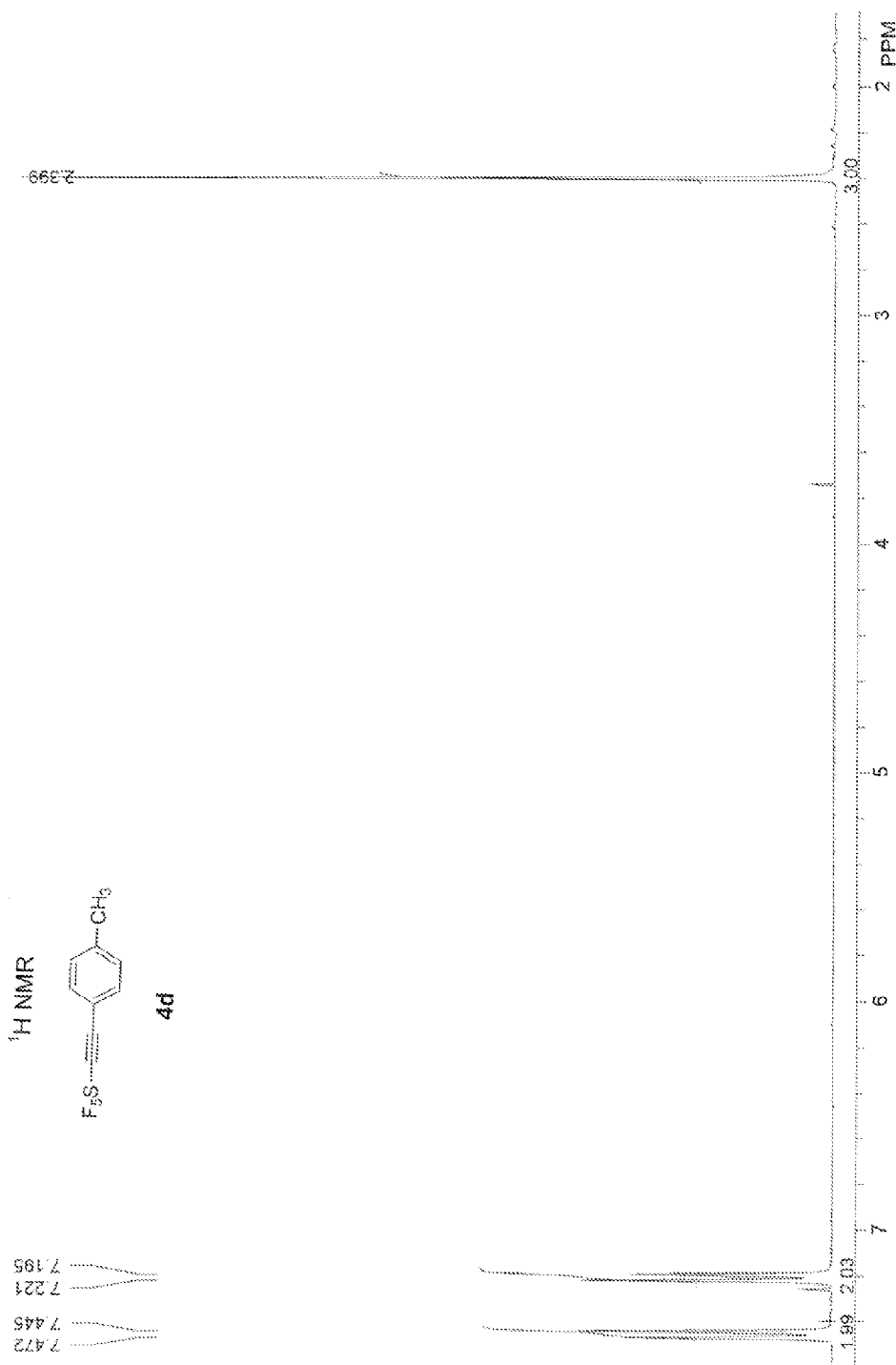
FIGS. 2A-2C present NMR spectra for compound 4d.
Figure 2B:
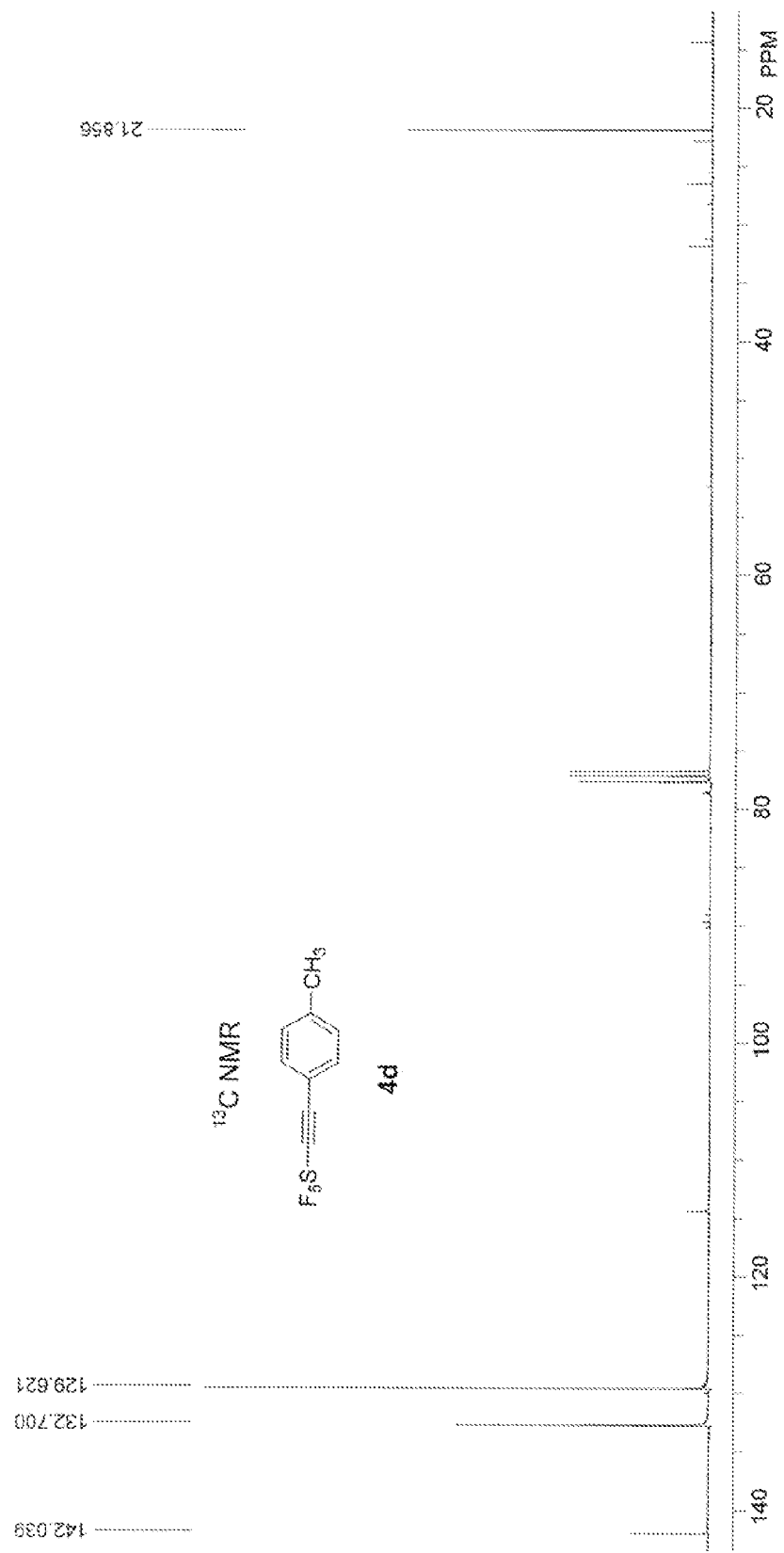
Figure 2C:
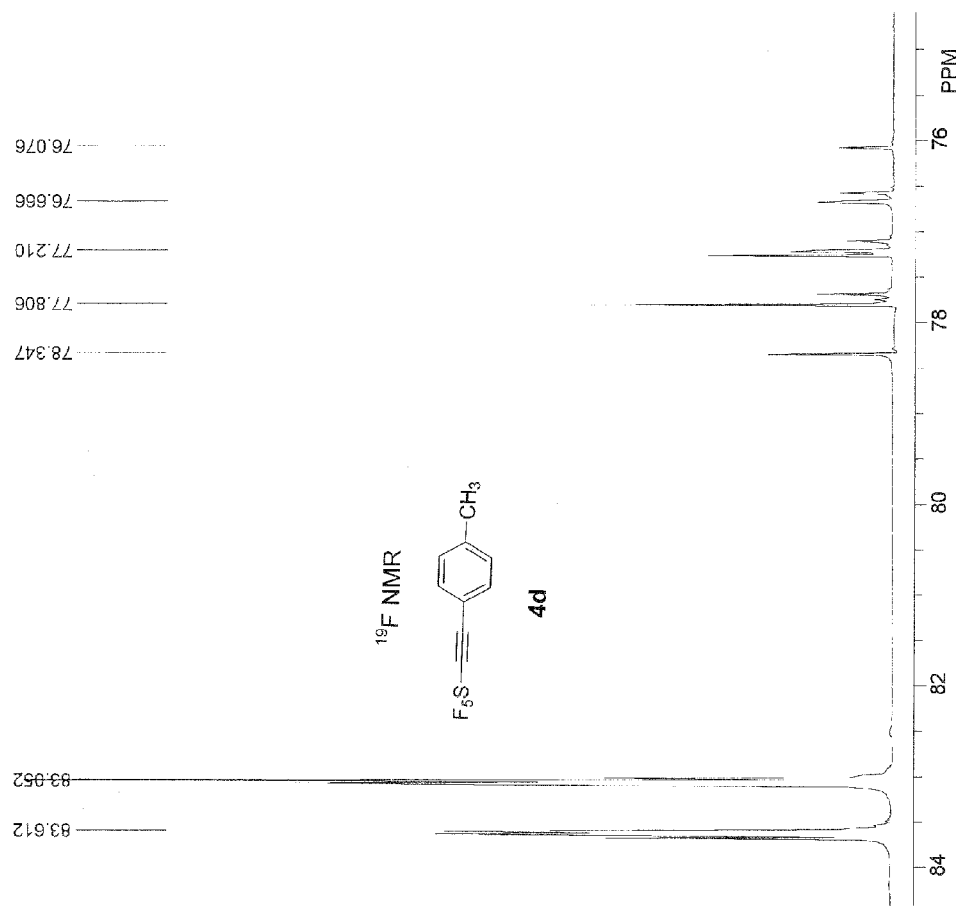
Figure 3B:
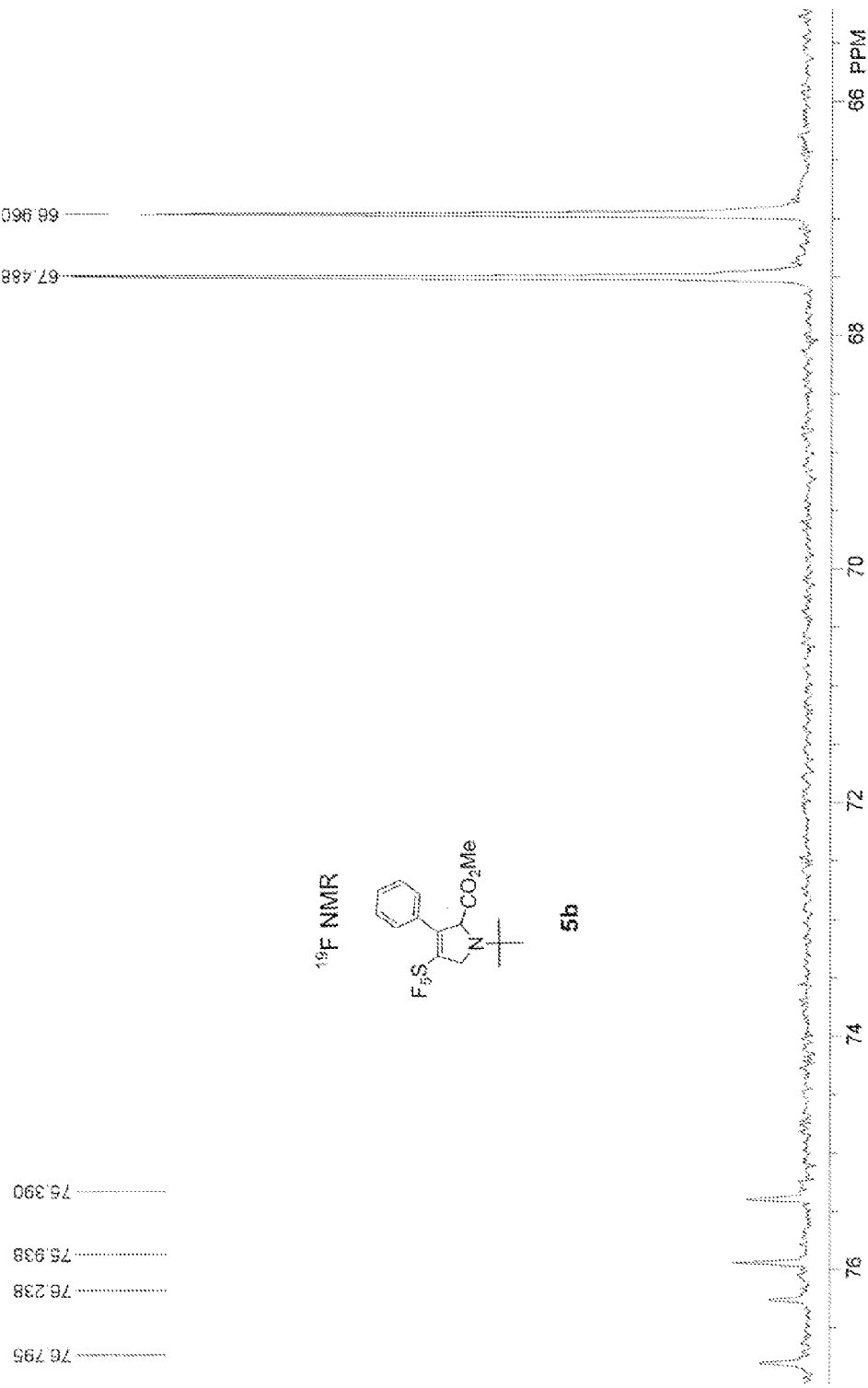
Figure 3C:
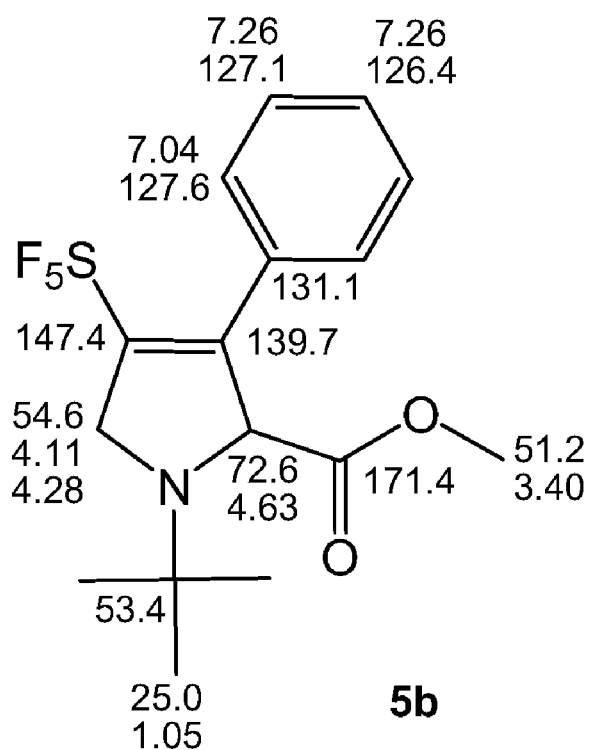
Figure 3D:
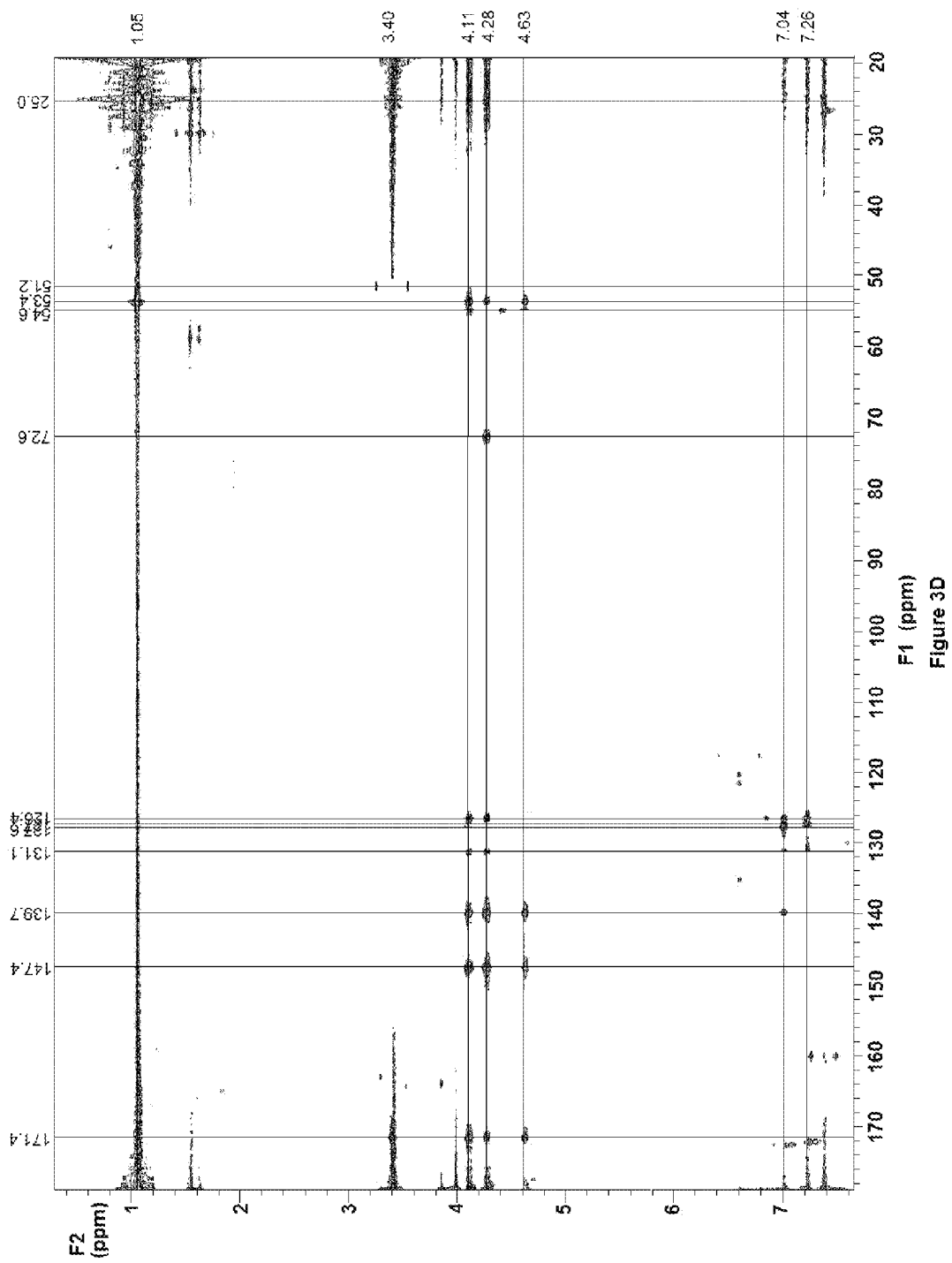
Figure 3E:
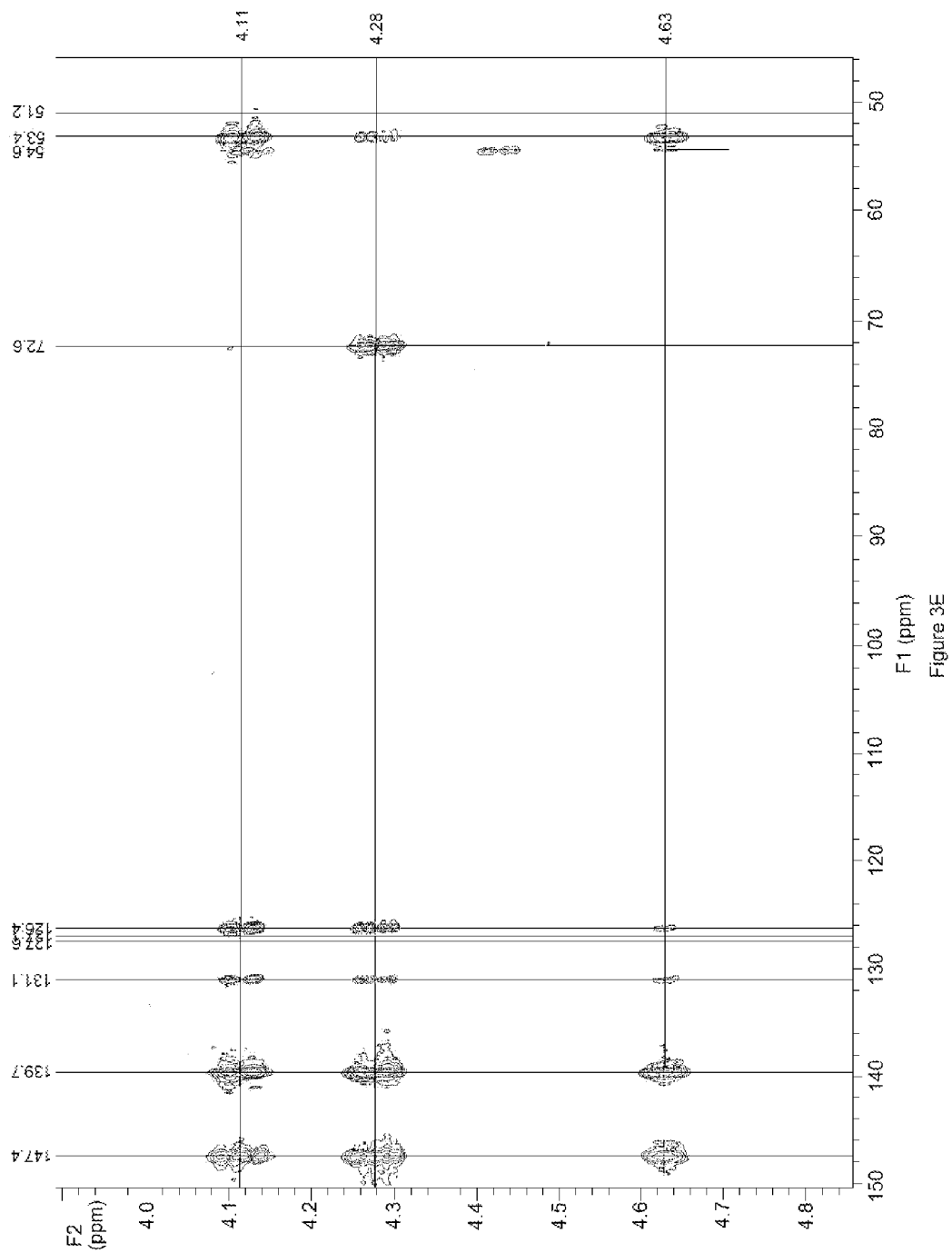
Figure 3F:
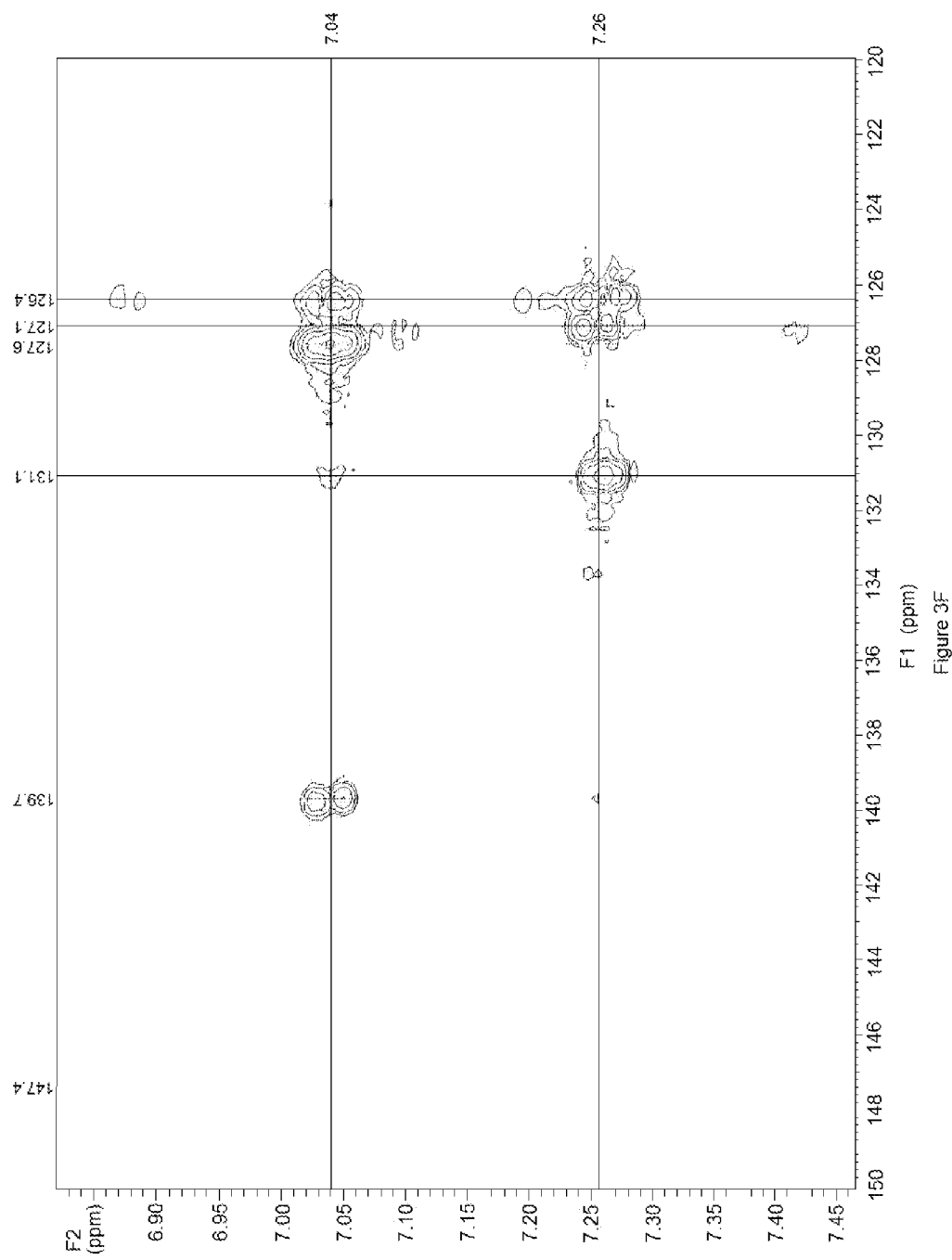
Figure 4A:
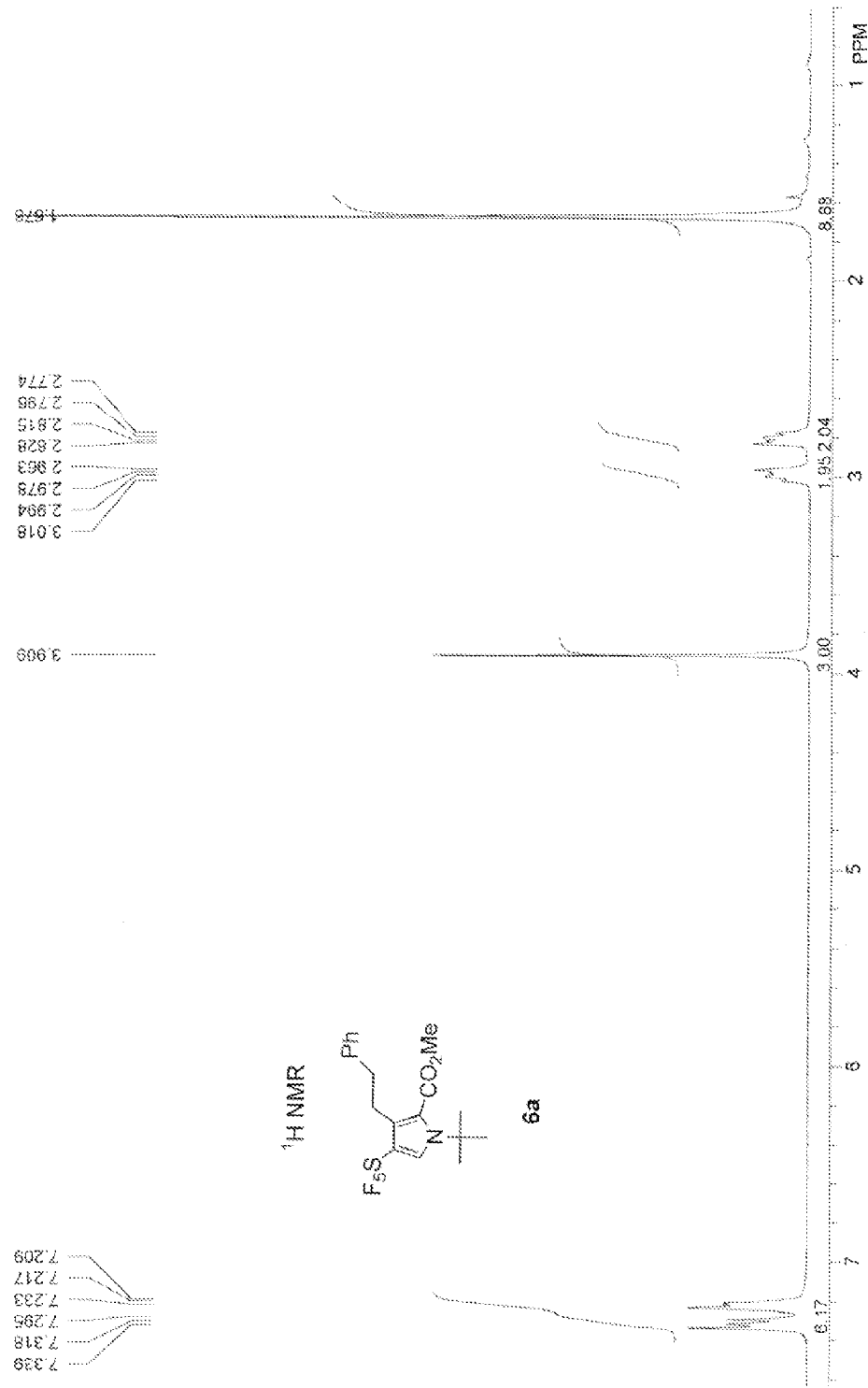
Figure 4B:
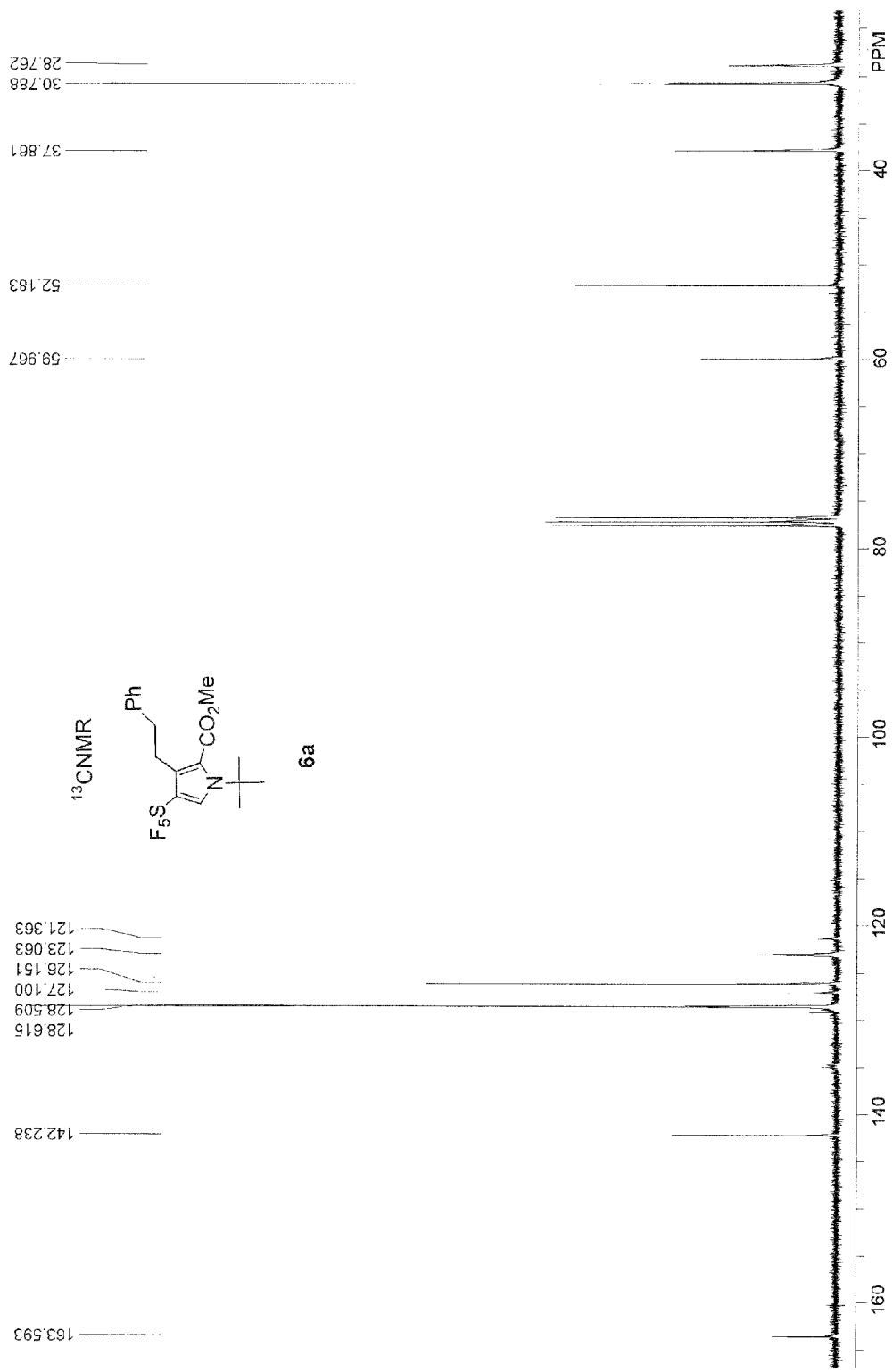
Figure 4C:
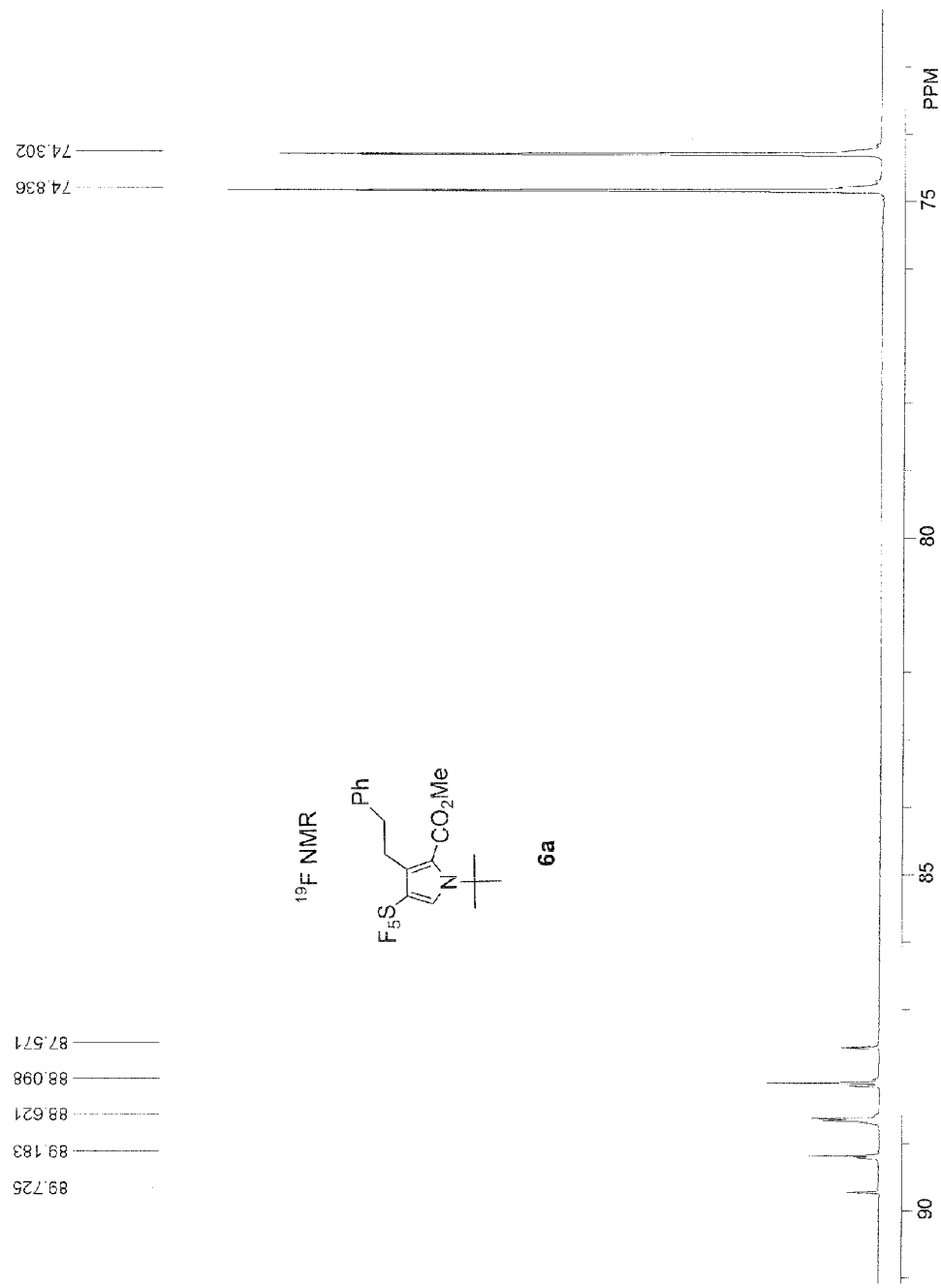

Embodiments of the subject invention are directed to pentafluorosulfanyl-substituted aromatic heterocycles—such as pyrroles and thiophenes—and non-aromatic 2,5-dihydro heterocycles—such as 2,5-dihydropyrroles (3-pyrrolines) and 2,5-dihydrothiophenes, along with further substituted analogues of each of the aforementioned compounds. These heterocycles bearing SF$_5$-groups are useful as intermediates for the development of novel pharmaceutical, agricultural, or other applications. These heterocycles bearing SF$_5$-groups are useful as specialty fluids, ligands, and monomers to form polymers, for example to form conjugated polymers such as polythiophenes and polypyrroles. For these applications the increased density and/or the electron withdrawing properties imparted by the SF$_5$ group is exploited. Other embodiments of the invention are directed to methods of synthesizing the pentafluorosulfanyl-substituted heterocycles and pentafluorosulfanyl-substituted 2,5-dihydro heterocycles.

The pentafluorosulfanyl-substituted heterocycles and pentafluorosulfanyl-substituted 2,5-dihydro heterocycles include, without limitation:

compound (A):

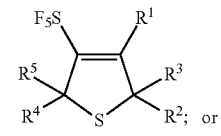

or compound (B):

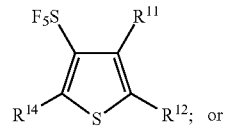

or compound (C):

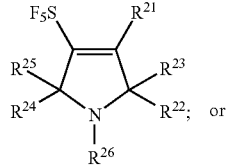

or

-continued compound (D):

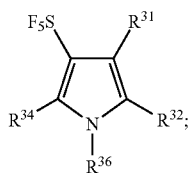

wherein $R^1$, $R^2$, $R^3$, $R^4$, $R^5$, $R^{11}$, $R^{12}$, $R^{14}$, $R^{21}$, $R^{22}$, $R^{23}$, $R^{24}$, $R^{25}$, $R^{26}$, $R^{31}$, $R^{32}$, $R^{34}$, and $R^{36}$ are, independently, hydrogen, halo, hydroxy, azido, cyanoato, isocyano, isocyanato, nitroxy, cyano, nitrosooxy, nitro, nitroso, thiocyanato, substituted or unsubstituted alkyl, substituted or unsubstituted alkenyl, substituted or unsubstituted alkynyl, substituted or unsubstituted aryl, substituted or unsubstituted heteroaryl, substituted or unsubstituted heterocyclic, substituted or unsubstituted alkoxy, substituted or unsubstituted aryloxy, substituted or unsubstituted carbonyl, substituted or unsubstituted carboxyl, substituted or unsubstituted carbonate, substituted or unsubstituted silyl, substituted or unsubstituted siloxy, substituted or unsubstituted peroxy, substituted or unsubstituted amino, substituted or unsubstituted imido, substituted or unsubstituted phospho, substituted or unsubstituted phosphine, substituted or unsubstituted phosphono, substituted or unsubstituted sulfanyl, substituted or unsubstituted carbonylsulfinyl, substituted or unsubstituted sulfonyl, substituted or unsubstituted sulfinyl, wherein "substituted" is used to refer to a chemical structure from which one or more hydrogens have been removed and each hydrogen replaced independently with a substituent selected from the group consisting of alkyl, alkenyl, alkynyl, aryl, heteroaryl, heterocyclic, a trialkylsilyl, siloxy, hydroxy, alkoxy, carbonyl, carboxyl, amino, thio, phospho, halo, oxo, and thiocarbonyl. Combined $R^2$ and $R^3$, $R^4$ and $R^5$, $R^{22}$ and $R^{23}$, and/or $R^{24}$ and $R^{25}$ can be oxo, thiocarbonyl or imino where the substituent can be unsubstituted or substituted.

Halo as used herein refers to a substituent that is —F (fluoro), —Cl (chloro), —Br (bromo), or —I (iodo). Hydroxy as used herein refers to —OH. Azido as used herein refers to a substituent —N=N$^+$=N$^-$. Cyanato as used herein refers to a substituent —O—C≡N. Isocyano as used herein refers to a substituent —N$^+$≡C$^-$. Isocyanato as used herein refers to a substituent —N=C=O. Nitroxy as used herein refers to a substituent —O—N$^+$(=O)—O$^-$. Cyano as used herein refers to a substituent —C≡N. Nitrosooxy as used herein refers to a substituent —O—N=O. Nitro as used herein refers to a substituent —N$^+$(=O)—O$^-$. Nitroso as used herein refers to a substituent —N=O. Thiocyanato as used herein refers to a substituent —S—C≡N.

Alkyl, as used herein, refers to a saturated hydrocarbon group of 1 to 20 carbons or more. Alkyl groups may be straight chain, branched, or cyclic, or any combination thereof where a plurality of branches and/or 3 carbon or larger rings can be at any position of the group and connected in any fashion. Alkenyl, as used herein, refers to a hydrocarbon group of 2 to 20 carbons or more that is saturated except for the presence of one or more carbon-carbon double bonds. Alkenyl groups may be straight chain, branched, or cyclic, or any combination thereof. Alkynyl, as used herein, refers to a hydrocarbon group of 2 to 20 carbons or more that is saturated except for the presence of one or more carbon-carbon triple bonds. Alkynyl groups may be straight chain, branched, or cyclic, or any combination thereof. Aryl, as used herein, refers to an aromatic group that is a hydrocarbon group of 6 to 20 carbons or more that consists of a single ring or a plurality of aromatic rings, which may be fused or not fused.

Heteroaryl, as used herein, refers to an aromatic group that contains one or more aromatic rings, which may be fused or not fused, of 5 to 20 atoms or more where one or more atoms of at least one of the aromatic rings is selected from the group consisting of N, O, S, P, and Se and where at least one atom of that ring is carbon. Heterocyclic, as used herein describe a substituent having one or more cyclic or ring structures where at least one ring contains one or more atoms selected from the group consisting of N, O, S, P, and Se and at least one carbon atom where that ring is not aromatic and has three atoms or more in the ring.

Alkoxy, as used herein, refers to an —OR group where R is any alkyl group as defined above. Aryloxy, as used herein, refers to an —OR group where R is any aryl or heteroaryl group as defined above.

Carbonyl, as used herein, refers to a —C(=O)—R' where R' is hydrogen (unsubstituted), alkyl, alkenyl, alkynyl, aryl, heteroaryl, or heterocycle such that the atom bonded to the carbon is hydrogen (formyl) or carbon. Carboxyl as used herein, refers to a —C(=O)—OR' where R' is hydrogen (unsubstituted), alkyl, alkenyl, alkynyl, aryl, heteroaryl, or heterocycle such that the atom bonded to the oxygen is hydrogen or carbon. Carboxylate as used herein refers to a substituent —O—C(=O)—R' where R' is hydrogen (unsubstituted), alkyl, alkenyl, alkynyl, aryl, heteroaryl, or heterocycle such that the atom bonded to the carbon is hydrogen or carbon.

Carbonate, as used herein, refers to —O—C(=O)—OR' where R' is hydrogen (unsubstituted), alkyl, alkenyl, alkynyl, aryl, heteroaryl, or heterocycle such that the atom bonded to the carbonyl is hydrogen or carbon. The carbonate can also be a thiocarbonate where one or more of oxygen atoms are replaced with sulfur atoms, as used herein.

Silyl as used herein refers to —(SiR'$_2$)$_n$R' where R' is independently hydrogen, alkyl, alkenyl, alkynyl, aryl, heteroaryl, or heterocycle and n is 1 to 20, such that atoms bonded to the silicon atom is hydrogen or carbon. Siloxy as used herein refers to —(OSiR'$_2$)$_n$R' or —(SiR'$_2$O)$_n$R' where R' is independently hydrogen, alkyl, alkenyl, alkynyl, aryl, heteroaryl, heterocycle, or SiR'$_3$ and n is 1 to 20.

Peroxy as used herein refers to a substituent —O—OR' where R' is hydrogen (unsubstituted), alkyl, alkenyl, alkynyl, aryl, heteroaryl, or heterocycle such that the atom bonded to the oxygen is hydrogen (hydroperoxy) or carbon (alkylperoxy or arylperoxy).

Amino as used herein refers to a substituent —NR'$_2$ where R' is independently hydrogen, alkyl, alkenyl, alkynyl, aryl, heteroaryl, or heterocycle such that the atom bonded to the nitrogen are hydrogen or carbon. Imido as used herein refers to a substituent —C(=NH)—OR' where R' is hydrogen, alkyl, alkenyl, alkynyl, aryl, heteroaryl, or heterocycle such that the atom bonded to the oxygen is hydrogen or carbon.

Phosphino as used herein refers to substituent —PR'$_2$ where R' is independently hydrogen, alkyl, alkenyl, alkynyl, aryl, heteroaryl, or heterocycle such that the atoms bonded to the phosphorous are hydrogen or carbon. Phosphono as used herein refers to a substituent —P(=O)(OR')$_2$ where R' is independently hydrogen, alkyl, alkenyl, alkynyl, aryl, heteroaryl, or heterocycle such that the atoms bonded to the oxygen are hydrogen or carbon. Phospho as used herein refers to a substituent —O—P(=O)(OR')$_2$ where R' is independently hydrogen, alkyl, alkenyl, alkynyl, aryl, heteroaryl, or heterocycle such that the atoms bonded to the oxygen are hydrogen or carbon.

Sulfanyl as used herein refers to a substituent —SR' where R' is hydrogen (unsubstituted), alkyl, alkenyl, alkynyl, aryl, heteroaryl, or heterocycle such that the atom bonded to the sulfur is hydrogen (thiol) or carbon. Carbonylsulfanyl as used herein refers to a substituent —S—C(═O)R' where R' is hydrogen (unsubstituted), alkyl, alkenyl, alkynyl, aryl, heteroaryl, or heterocycle such that the atom bonded to the carbonyl carbon is hydrogen or carbon. Sulfonyl as used herein refers to a substituent —S(═O)$_2$—R' where R' is hydrogen (unsubstituted), alkyl, alkenyl, alkynyl, aryl, heteroaryl, or heterocycle such that the atom bonded to the sulfur is hydrogen or carbon. Sulfo as used herein refers to a substituent —S(═O)$_2$—OR' where R' is hydrogen (unsubstituted), alkyl, alkenyl, alkynyl, aryl, heteroaryl, or heterocycle such that the atom bonded to the oxygen is hydrogen or carbon. Sulfinyl as used herein refers to a substituent —S(═O)—R' where R' is hydrogen (unsubstituted), alkyl, alkenyl, alkynyl, aryl, heteroaryl, heterocycle or halogen such that the atom bonded to the sulfur is hydrogen, carbon, or a halogen.

Oxo as used herein refers to a substituent ═O that bonds to the heterocycle ring as a substituent to the SF$_5$ substituted heterocycle ring or as a substituent of a substituent to the SF$_5$ substituted heterocycle ring. Thiocarbonyl as used herein refers to a substituent ═S that bonds to the heterocycle ring as a substituent to the SF$_5$ substituted heterocycle ring or as a substituent of a substituent to the SF$_5$ substituted heterocycle ring. Imino as used herein refers to a substituent ═NR' that bonds to the heterocycle ring as a substituent to the SF$_5$ substituted heterocycle ring or as a substituent of a substituent to the SF$_5$ substituted heterocycle ring where R' is hydrogen, alkyl, alkenyl, alkynyl, aryl, heteroaryl, heterocycle or halogen such that the atom bonded to the nitrogen is hydrogen or carbon.

In a specific embodiment, $R^2$, $R^3$, $R^4$, and $R^5$ of compound A are hydrogen. In yet another specific embodiment, $R^2$, $R^3$, $R^4$, and $R^5$ of compound A are hydrogen while $R^1$ is aryl, alkyl, arylalkylene, or alkylarylene.

In a specific embodiment, $R^{12}$ and $R^{14}$ of compound B are hydrogen. In yet another specific embodiment, $R^{12}$ and $R^{14}$ of compound B are hydrogen while $R^{11}$ is aryl, alkyl, arylalkylene, or alkylarylene.

In a specific embodiment, $R^{23}$, $R^{24}$, and $R^{25}$ of compound C are hydrogen. In yet another specific embodiment, $R^{23}$, $R^{24}$, and $R^{25}$ of compound C are hydrogen, and $R^{22}$ is substituted carboxyl. In still another specific embodiment, $R^{23}$, $R^{24}$, and $R^{25}$ of compound C are hydrogen, $R^{22}$ is a substituted carboxyl group, such as methylcarboxyl, and $R^{26}$ is a tert-alkyl group, such as tent-butyl, or hydrogen. In an embodiment, $R^{21}$ is aryl, alkyl, arylalkylene, or alkylarylene.

In a specific embodiment, $R^{34}$ of compound D is hydrogen. In yet another specific embodiment, $R^{34}$ of compound D is hydrogen, and $R^{32}$ is substituted carboxyl. In still another specific embodiment, $R^{34}$ of compound D is hydrogen, $R^{32}$ is a substituted carboxyl group, such as methylcarboxyl, and $R^{36}$ is a tert-alkyl group, such as tent-butyl, or hydrogen. In an embodiment, $R^{31}$ is aryl, alkyl, arylalkylene, or alkylarylene.

In specific embodiments, the compounds include 3-pentafluorosulfanyl-4-p-tolyl-dihydrothiophene (compound 1); 3-pentafluorosulfanyl-4-p-tolyl-thiophene (compound 2); methyl 1-tert-butyl-4-pentafluorosulfanyl-3-phenyl-2,5-dihydro-2H-pyrrole-2-carboxylate (compound 5b); methyl 1-tert-butyl-4-pentafluorosulfanyl-3-(2-phenyl ethyl)pyrrole-2-carboxylate (compound 6a); methyl 1-tert-butyl-4-pentafluorosulfanyl-3-phenylpyrrole-2-carboxylate (compound 6b); methyl 1-tert-butyl-4-pentafluorosulfanyl-3-butylpyrrole-2-carboxylate (compound 6c); methyl 1-tert-butyl-4-pentafluorosulfanyl-3-p-tolylpyrrole-2-carboxylate (compound 6d); and methyl 4-pentafluorosulfanyl-3-(2-phenylethyl)pyrrole-2-carboxylate (compound 7).

As substituents can be further substituted, they can be referred to as canonical substituents, combination substituents, combined substituents, and substituted substituents. For example, if the canonical substituent includes alkyl and simple aryl, then p-tolyl can be regarded as a combined substituent. The p-tolyl substituent is simple aryl (in this case, phenyl) substituted with an alkyl (in this case, methyl). The primary substituent is the substituent that attaches directly to the parent SF$_5$ substituted heterocycle. A secondary substituent is a substituent that is substituted onto a primary substituent. For example, in the case of p-tolyl, the primary component substituent is simple aryl (in this case, phenyl) and the secondary component substituent is alkyl (in this case, methyl). In like manner, a tertiary substituent is a substituent on a secondary substituent. More generally, the substituents can be given a rank $N^o$ that is substituted onto an $(N-1)^o$ substituent.

Each substituent can independently contain 1, 2, 3, 4, 5, 6, 7, 8, 9, 10, 11, 12, 13, 14, 15, 16, 17, 18, 19, 20, 21, 22, 23, 24, or more carbon atoms, for example a primary substituent may have 6 carbons, a second primary substituent may have 8 carbons, and a secondary substituent may have 3 carbons. Suitable heteroatoms in substituents include, without limitation, N, O, S, P, and Se.

Other embodiments of the subject invention are directed to the synthesis of the above compounds according to embodiments of the invention where ring formation involves addition of a 1,3-dipolar species, or its synthetic equivalent. In one embodiment, an SF$_5$ substituted alkyne is converted to an SF$_5$ substituted dihydrothiophene, as shown below in Scheme I:

SCHEME I

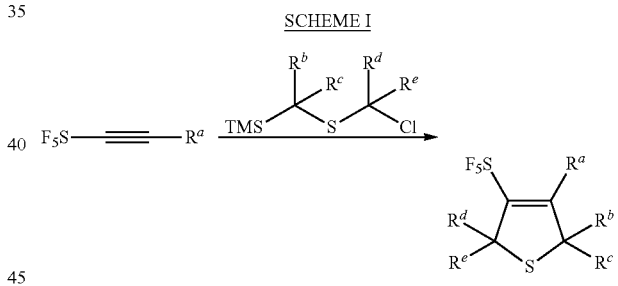

wherein the reaction of Scheme I takes place in the presence of TBAF (tetra-n-butylammonium fluoride) or a similar fluoride or other nucleophilic reagent towards a silane that is coupled with a tetraalkylammonium or other cation that provides adequate solubility in a non-protic organic solvent. The reagents are contacted generally with agitation, for a sufficient amount of time for the reaction to proceed to completion or equilibrium. For example, the mixture can be stirred for about 1, 2, 3, 4, or more hours. In one embodiment, mixing takes place at room temperature (typically about 20° C. to about 23° C.). The reaction may be quenched by addition of water or other protic solvents, and the product can be purified by column chromatography, distillation, crystallization, or other common separation technique as appropriate for a given product based on its crystallinity, boiling point, or any other property and with regard to such properties of any side products or unconverted reagents. In various embodiments of the invention $R^a$ can be aryl, alkyl, arylalkylene, or alkylarylene.

In one embodiment, $R^b$, $R^c$, $R^d$, and $R^e$ are all hydrogen. In another embodiment the chloromethyl trimethylsilyl methylsulfide is substituted with 1 or more substituents on one or both of the carbons alpha to the sulfur (i.e., one or more of $R^b$, $R^c$, $R^d$, and $R^e$ are non-hydrogen). In one embodiment, $R^a$, $R^b$, $R^c$, $R^d$, and $R^e$ are the same as $R^1$, $R^2$, $R^3$, $R^4$, and $R^5$ of compound A, respectively. Alternatively, $R^a$, $R^b$, $R^c$, $R^d$, and $R^e$ are groups that may be converted to $R^1$, $R^2$, $R^3$, $R^4$, and $R^5$, respectively, by methods known in the art or disclosed herein. In one embodiment, at least one of $R^b$, $R^c$, $R^d$, and $R^e$ is electron-withdrawing, such as ester, nitro, cyano, or other electron-withdrawing groups known in the art.

Without being bound to any theory, the reaction is consistent with the involvement of a thiocarbonyl ylide intermediate, as shown below as a pair of resonance structures, generated by loss of $TMS^+$, possibly as TMSF, and $Cl^-$. Accordingly, alternative methods of preparing thiocarbonyl ylides or their equivalents may be used to prepare a species that reacts with the $SF_5$ substituted alkyne. See, for example, Kellogg Tetrahedron 32:2165-2184 (1976). Alternative methods of generating a thiocarbonyl ylide for reaction with the $SF_5$ substituted alkyne are those where a carbene reacts with a thioketone or aldehyde.

Thiocarbonyl Ylide Resonance Structures:

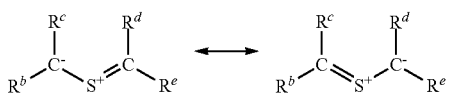

Although Scheme I depicts formation of the thiacyclopentene with $R^d$ and $R^e$ substituted at the 2-position of the ring and $R^b$ and $R^c$ substituted at the 5-position, ring formation can proceed such that $R^b$ and $R^c$ are at the 2-position and $R^d$ and $R^e$ are at the 5-position or a mixed product where either $R^b$ and $R^c$ or $R^d$ and $R^e$ are at the 2-position relative to the $F_5S$ being at the 3-position. Scheme I is understood to refer to these two possibilities generically. In general, the two resonance structures are not of equal energy and population when substitution is not symmetric about the central sulfur. The proportion of the $R^b$ and $R^c$ at the 2-position reflects the nature of the substituents $R^b$ through $R^e$ and need not be indicative of which substituents are alfa to the TMS as shown in Scheme I as can be appreciated by one skilled in the art.

Embodiments of the subject invention are directed to oxidizing a $SF_5$ substituted thiacyclopentene as prepared by the method illustrated in Scheme I with an appropriate reagent or reagents to obtain the corresponding $F_5S$ substituted thiophene. Any thiacyclopentene prepared by Scheme I that has at least one hydrogen at the 2-position and at least one hydrogen at the 5-position of the ring (relative to $F_5S$ at the 3-position) or an equivalent substituent toward oxidation (removal in the presence of an oxidant) may be oxidized to the corresponding thiophene as indicated below in Scheme II:

SCHEME II

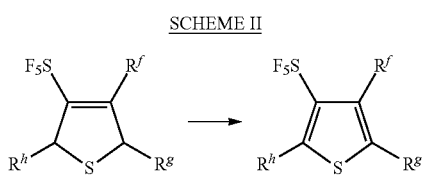

In one embodiment, the thiacyclopentene is reacted with sulfuryl chloride. In another embodiment, the thiacyclopentene is contacted with the sulfuryl chloride at a temperature of 10, 0, -10, -20, or -30° C. or less. The reaction is typically carried out in solution, for example, a dichloromethane (DCM) solution. Mixing of the reagents may occur with agitation for a sufficient amount of time for the reaction to proceed to completion or equilibrium. In a one embodiment the mixture is stirred for about up to 10, 20, 30, 40, 50, or 60 or more minutes. One or the other reagent, for example, the sulfuryl chloride, can be added slowly, for example dropwise or with a pump, over a period of time, for example 1, 2, 3, 5, 10, 15, 20 or more minutes as needed to achieve a reasonably high conversion. The reaction may be terminated by water or other protic solvent. As needed, the organic phase may be dried using $Na_2SO_4$ or other desiccant, such as calcium chloride, calcium sulfate, magnesium sulfate, or potassium carbonate. The dried solvent may be evaporated and the thiophene product purified by column chromatography, distillation, crystallization or other methods permitting the isolation of the desired thiophene, as is appropriate for its structure.

In one embodiment, $R^f$ is aryl, alkyl, arylalkylene, or alkylarylene. In one embodiment, $R^h$ and $R^g$ are both hydrogen. In one embodiment, $R^f$ is aryl, alkyl, arylalkylene, or alkylarylene, and $R^h$ and $R^g$ are both hydrogen.

An embodiment of the subject invention is a method for the synthesis of an $SF_5$ substituted pyrroline compound from an $SF_5$ substituted alkyne and a 1,3-dipolar species or its equivalent, for example an aziridine compound, or, for example N-(methoxymethyl)-N-(trimethylsilylmethyl)benzylamine, as shown for an aziridine in Scheme III:

SCHEME III

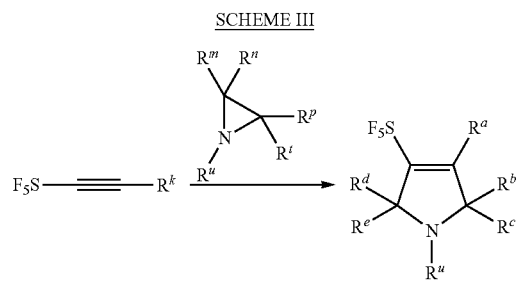

In one embodiment of the invention, the reaction is carried out at an elevated temperature, such as 45, 60, 75, 90, 105, 120, 135, 150, 165, 180, 195° C. or more. The reaction can be carried out in a solvent, for example xylene. Reaction times of 1, 3, 6, 9, 12, 24, 48, or 72, or more hours may be employed as needed. In one embodiment, the reaction time is about 16-32 hours at 120-150° C. Non-limiting examples of aziridine compounds are available from Sigma-Aldrich (St. Louis, Mo.) and reported at PubChem.

In one embodiment, $R^k$ is aryl, alkyl, arylalkylene, or alkylarylene. In one embodiment, at least one of $R^p$ and $R^t$ and at least one of $R^m$ and $R^n$ is hydrogen. In one embodiment, the aziridine ring is substituted with 1 or more substituents on one or both of the ring carbons (i.e., one or more of $R^m$, $R^n$, $R^p$, and $R^t$ are non-hydrogen). Accordingly, pyrrolines are produced wherein the ring can be monosubstituted, disubstituted, trisubstituted or tetrasubstituted. In one embodiment, at least one of $R^m$, $R^n$, $R^p$, and $R^t$ is electron-withdrawing, such as carboxyl, nitro, cyano, or other electron-withdrawing groups known in the art. Substituents $R^k$, $R^m$, $R^n$, $R^p$, $R^t$, and $R^u$ can be $R^{21}$, $R^{22}$, $R^{23}$, $R^{24}$, $R^{25}$, and $R^{26}$, respectively of the compounds described above.

Alternatively, $R^k$, $R^m$, $R^n$, $R^p$, $R^t$, and $R^u$ can be $R^{21}$, $R^{24}$, $R^{25}$, $R^{22}$, $R^{23}$, and $R^{26}$, respectively, as two possible intermediate structures, which are not of equal energy and population when substitution is not symmetric about the nitrogen of the aziridine, are potentially involved in the reaction. The proportion of the $R^p$ and $R^t$ at the 2-position relative to $F_5S$ at the 3-position reflects the nature of the substituents $R^n$ through $R^t$, as can be appreciated by one skilled in the art.

Without being bound by any theory, the reaction product is consistent with a mechanism where the $F_5S$ substituted alkyne reacts with an azomethine ylide intermediate, the structure of which is shown below, generated by ring-opening of the aziridine compound. Accordingly, alternative methods of preparing azomethine ylides may be used to prepare the species that reacts with the $SF_5$ substituted alkyne. See, for example, Nájera & Sansano *Current Organic Chemistry* 7:1105-1150 (2003). Alternative methods of generating an azomethine ylide for reaction with the $SF_5$ substituted alkyne are those using a decarboxylative method, for example using 5-oxazolidinones as thermal precursors.

Azomethine Ylide Resonance Structures:

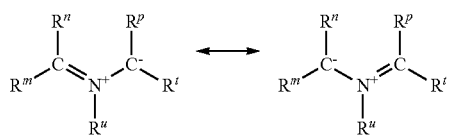

Another embodiment of the invention is directed to the oxidation of $SF_5$ substituted pyrrolines to pyrroles. For example, any pyrrolines produced by Scheme III that have at least one hydrogen at ring carbon 2 and at least one hydrogen at ring carbon 5 or an equivalent toward oxidation may be converted to a pyrrole as shown in Scheme IV:

SCHEME IV

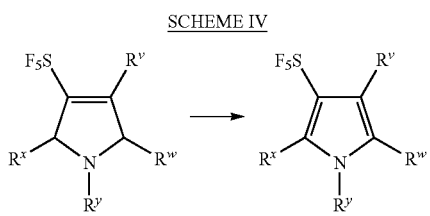

wherein reaction takes place in contact with an oxidizing agent, such as dichloro-dicyano-quinone (DDQ). The DDQ can be mixed with the pyrroline in solution, for example, a carbon tetrachloride solution. Agitation can be employed to enhance mixing of reagents. In one embodiment, the reaction may be carried out at room temperature (about 20° C. to about 23° C.) for a sufficient period of time to until the reaction reaches an acceptable conversion. Reaction times of up to about 1, 2, 3, 4, 5, or 6 hours or more may be used. After reaction, the solvent may be removed and the product purified by column chromatography, distillation, crystallization, or other method depending on the specific $SF_5$ substituted pyrrole formed.

In an embodiment of the invention where a hydrogen is desired at $R^{26}$ or $R^{36}$ of compounds C or D, respectively, the method further comprising replacement of a non-hydrogen substituent $R^u$ as indicated in Scheme III and/or non-hydrogen substituent $R^y$ as indicated in Scheme IV, with hydrogen is shown in Scheme V.

SCHEME V

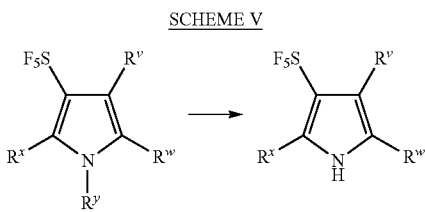

The reaction of Scheme V may be accomplished, for example, by use of catalytic quantities of triflic acid ($CF_3SO_3H$) or other equivalent strong acids in methylene chloride or other strong acid inert solvents when $R^u$ or $R^y$ is susceptible to removal by the acid. For example, triflic acid may be employed in a catalytic amount. In one embodiment, the reaction can be carried out at room temperature (about 20° C. to about 23° C.) for a sufficient period of time to achieve a good conversion or completion. Reaction times of up to about 1, 2, 3, 4, 5, or 6 hours or more may be used. Agitation of the reaction solution can be effected. After reaction, the solvent may be removed by distillation and the product purified by column chromatography, distillation, crystallization or other method appropriate for the specific product.

This replacement process may be used to replace non-hydrogen $R^u$ with hydrogen on pyrrolines and non-hydrogen $R^y$ with hydrogen on pyrroles. The process extends to pyrroles and pyrrolines wherein the ring carbon(s) at position 2 or 5 or both are monosubstituted, and to pyrrolines wherein the ring carbon(s) at position 2 or 5 or both are disubstituted. Accordingly, the procedure for replacement of $R^u$ or $R^y$, which acts as a nitrogen protecting substituent, with hydrogen is effective for the full scope of compounds taught herein. In an embodiment of the invention, $R^u$ or $R^y$ is t-butyl or other tri-alkyl substituted carbons. In other embodiments of the invention other groups capable of forming a relatively stable carbocation, such as a benzylic or allylic group can be substituents $R^u$ or $R^y$. Any method of "deprotecting" nitrogen of the pyrroles and pyrrolines known in the art may be employed. For example, methods of removing alkoxycarbonyl groups from heterocycles are known in the art.

Various enantiomeric forms of the compounds according to embodiments of the subject invention may be isolated according to methods known to the skilled artisan. The SF; substituted compounds and intermediate products prepared according to embodiments of the invention can be neutralized or dried as needed. For example, neutralization can be performed by the addition of a sufficient amount of sodium bicarbonate ($HNaCO_3$) or acid, for example hydrochloric acid (HCl) to an acidic product or product mixture or a basic product or product mixture, respectively, in solution or neat. Drying can be performed using a suitable desiccant, for example, $MgSO_4$. Purity and/or analysis of the compounds according to embodiments of the invention may be determined using any technique or combination thereof known in the art including without limitation nuclear magnetic resonance (NMR) analysis and chromatography, for example thin layer chromatography (TLC), gas chromatograph (GC), or liquid chromatography (LC). In the above-described compounds and intermediate products of the subject invention, bond line notation has been used. Thus, the skilled artisan would understand that although not always depicted, hydrogen atoms are present in an amount to satisfy the requirement that each carbon atom has four bonds.

The methods disclosed herein for preparing $SF_5$-substituted heterocycles have proven to be far superior to certain known methods for preparing pyrroles [Joule & Mills *Heterocyclic Chemistry* 1995], such as the Paal-Knorr synthesis, the Knorr synthesis, the Hantzsch synthesis, and the van Leusen synthesis, which have been unsuccessful for preparation of $F_5S$ substituted heterocycles according to an embodiment of the invention.

The terms "comprising", "consisting of", and "consisting essentially of" are defined according to their standard meaning and may be substituted for one another throughout the instant application in order to attach the specific meaning associated with each term.

As used in this specification and the appended claims, the singular forms "a", "an", and "the" include plural reference unless the context clearly dictates otherwise. Thus, for example, a reference to "an alkyne" includes more than one such alkyne, a reference to "the method" includes more than one such method, and the like.

Following are examples which illustrate procedures for practicing the invention. These examples should not be construed as limiting. All percentages are by weight and all solvent mixture proportions are by volume unless otherwise noted.

Materials and Methods

Preparation of Starting Materials

Pentafluorosulfanyl alkynes, 4, are readily available by the addition of $SF_5Cl$ to terminal alkynes, followed by base-catalyzed elimination of HCl. Preparation of such compounds is taught by Dolbier et al, *J Fluorine Chem* 127:1302-1310; Mitani & Dolbier, WO 07/106,818; and Lal & Minnich, U.S. Pat. No. 6,479,645, and these disclosures are incorporated herein by reference in their entireties. Non-limiting examples of pentafluorosulfanyl alkynes are those in which R is —$CH_2CH_2Ph$ (designated 4a), -Ph (4b), n-butyl (4c), or p-tolyl (4d).

Preparation of $SF_5$-alkynes

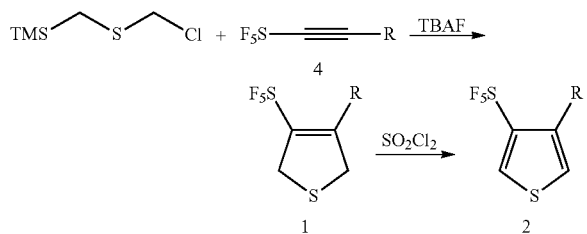

Aziridine 3 and $SF_5$-alkyne starting materials 4b and 4c were prepared according to the literature preparations: La Porta et al. *Synthesis* 1994(3):287-290 and Dolbier et al. *J Fluorine Chem* 127:1302-1310, which are incorporated herein by reference.

Alkynes 4a and 4d were prepared as follows. Into a flask equipped with a dry ice reflux condenser were added at −40° C., 20 mL of anhydrous hexane, alkyne (3-4 mmol) and $SF_5Cl$ (1.2 equiv). The solution was stirred at this temperature for 10 min, and $Et_3B$ (0.1 equiv., 1M in hexane) was added slowly using a syringe. The solution was stirred for 1 h at −30° C., and then warmed to RT. The mixture was hydrolyzed with aqueous $NaHCO_3$ and the organic phase dried with $MgSO_4$. After removing the solvent, 20 mL of DMSO was added to the residue along with 5 equiv LiOH. The solution was stirred at RT for 2 h, after which the mixture was poured into ice water and neutralized with 2M HCl. The product was extracted with ether twice, dried with $MgSO_4$, and finally purified by column chromatography.

4a (43%): $^1H$ NMR, δ 2.55-2.62 (m, 2H), 2.85-2.90 (t, J=10 Hz, 2H), 7.18-7.33 (m, 5H); $^{13}C$ NMR, δ 20.41, 33.52, 127.03, 128.50, 128.81, 139.20; $^{19}F$ NMR, δ 77.4 (p, J=158 Hz, 1F), 82.6 (d, J=160 Hz, 4F).

4d (45%): $^1H$ NMR, δ 2.40 (s, 3H), 7.20-7.22 (d, J=7.8 Hz, 2H), 7.44-7.47 (d, J=7.8 Hz, 2H); $^{13}C$ NMR, δ 21.86, 129.70, 132.72, 142.12; $^{19}F$ NMR, δ 77.3 (p, J=162 Hz, 1F), 88.05 (d, J=177 Hz, 4F).

Characterization of Compounds

NMR spectra were obtained in $CDCl_3$ using TMS and $CFCl_3$ as the internal standards for $^1H/^{13}C$ NMR and $^{19}F$ NMR respectively; melting points were uncorrected.

EXAMPLE 1

Dihydrothiophenes and Thiophenes

Reactions of $SF_5$-alkynes have been carried out as illustrated below for the synthesis of $SF_5$-substituted thiophenes.

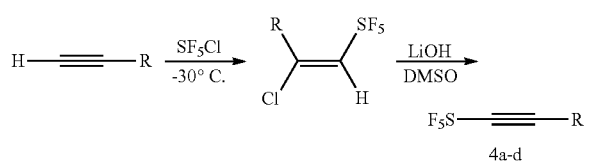

TBAF (1.0M in THF, 1.3-5 equiv) was added to a mixture of chloromethyl trimethylsilylmethylsulfide (1.3-5 equiv) and $SF_5$-alkynes where R is para-tolyl (1 equiv) 4d in THF at room temperature (RT). After stirring for several hours (monitored by $^{19}F$-NMR), the reaction was quenched using water, submitted to column, and chromatography 1d was obtained as a white solid in 67% yield.

A solution of 1d in DCM was cooled to −30° C., and sulfuryl chloride (2 equiv) was added slowly in 10 minutes. After stirring for another 30 minutes, the reaction was terminated by water and the organic phase was dried by $Na_2SO_4$. The solvent was evaporated and the residue purified by column to give chromatography 2d as white solid.

3-pentafluorosulfanyl-4-p-tolyl-dihydrothiophene, compound 1d: $^1HNMR$ ($CDCl_3$), δ2.36 (s, 3H), 3.99 (s, 2H), 4.31-4.34 (t, J=5.1 Hz, 2H), 7.06-7.08 (d, J=8.1 Hz, 2H), 7.17-7.19 (d, J=7.8 Hz, 2H); $^{19}FNMR$, δ83.12 (p, J=153 Hz, 1F), 67.05 (d, J=163 Hz, 4F).

3-pentafluorosulfanyl-4-p-tolyl-thiophene, compound 2d: $^1HNMR$ ($CDCl_3$), δ2.40 (s, 3H), 7.07 (m, 1H), 7.19 (s, 4H), 7.87-7.88 (d, J=3.9 Hz, 1H); $^{13}CNMR$, δ21.43, 124.93, 127.90, 128.50, 129.64, 133.09, 137.85, 139.77, 150.65 (m); $^{19}FNMR$, δ84.27 (p, J=167 Hz, 1F), 72.55 (d, J=162 Hz, 4F).

EXAMPLE 2

Pyrrolines and Pyrroles

Cycloadditions of azomethine ylides to $SF_5$-alkynes, followed by oxidation of the intermediate pyrrolines, have been successfully employed for the synthesis of $SF_5$-pyrroles, as shown below. The aziridine precursor 3 advantageously facilitates later removal of the tert-butyl group from the pyrrole nitrogen, if desired. The azomethine ylide form of the aziridine ester 3 is also shown.

Preparation of SF$_5$-pyrroles

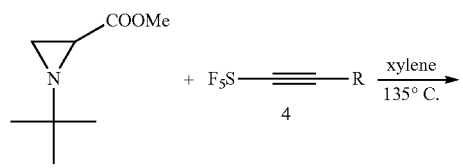

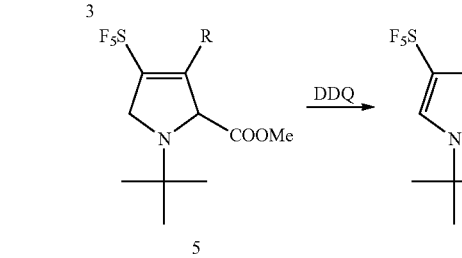

6a, CH$_2$CH$_2$Ph (60%);
6b, Ph (53%)
6c, n-Butyl (54%);
6d, p-tolyl (78%)

Azomethine Ylide Form of Aziridine Ester

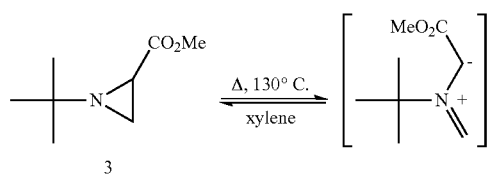

The pentafluorosulfanyl alkynes, 4, were readily available by the addition of SF$_5$Cl to terminal alkynes, followed by base-catalyzed elimination of HCl as illustrated above. Preparation of such compounds is taught by Dolbier et al., *J Fluorine Chem* 127:1302-1310; Mitani et al., WO 07/106,818; and Lal et al., U.S. Pat. No. 6,479,645, and incorporated herein by reference in their entireties. Non-limiting examples of pentafluorosulfanyl alkynes are those in which R is —CH$_2$CH$_2$Ph 4a, -Ph 4b, n-butyl 4c, or p-tolyl 4d. When such alkynes were allowed to react with aziridine ester 3 as depicted above, SF$_5$-substituted pyrrolines, 5, were obtained. Pyrroline 5b was isolated and characterized and its regiochemistry of cycloaddition determined. Other pyrrolines were not fully characterized, but were isolated and subjected to oxidation by DDQ to form the tent-butyl pyrroles 6 (53 to 78% yield), which were fully characterized.

Procedure for Preparation of Pyrroles 6a-d.

A mixture of 3 (2.05 mmol, 3 eq), 4 (0.68 mmol, 1 eq) and 2.5 ml xylene was heated at about 135° C. for 24 h (monitored by NMR). Product 5 was separated from excess 3 by flash chromatography, and then 5 mL CCl$_4$ and 310 mg DDQ were added to the crude 5 at RT and the mixture stirred for 3 h (monitored by TLC). The solvent was then removed by distillation, and the residue submitted to column chromatography to obtain 6 as a white solid.

Although the intermediate dihydropyrroles were not generally isolated, but were directly converted to the respective pyrroles by treatment with DDQ, the structure of one dihydropyrrole intermediate, 5b, was demonstrated unambiguously by NMR analysis prior to its oxidative conversion to pyrrole 6b.

Methyl 1-tert-butyl-4-pentafluorosulfanyl-3-phenyl-2,5-dihydro-2H-pyrrole-2-carboxylate, compound 5b: $^1$H NMR, δ 1.12 (s, 9H), 3.48 (s, 3H), 4.18 (dd, J=14.1, 5.1 Hz, 1H), 4.35 (dd, J=14.1. 6.6 Hz, 1H), 4.70 (m, 1H), 7.10 (m, 2H), 7.34 (m, 3H); $^{13}$C NMR, δ 25.0, 51.2, 53.4, 54.6 (C-5), 72.6 (C-2), 126.4, 127.1, 127.6, 131.1, 139.7 (C-3), 147.4 (SF$_5$—C), 171.4 (C=O); $^{19}$F, δ +67.2 (d, J=148 Hz, 4F), +76.1 (m, 1F).

Methyl 1-tert-butyl-4-pentafluorosulfanyl-3-(2-phenylethyl)pyrrole-2-carboxylate, compound 6a: (60%) mp 115-117° C.; $^1$H NMR, δ 1.67 (s, 9H), 2.77-2.83 (dd, J=6.6 & 4.5 Hz, 2H), 2.96-3.02 (dd, J=6.6 & 4.5 Hz, 2H), 3.91 (s, 3H), 7.21-7.34 (m, 6H); $^{13}$C NMR, δ 28.83, 30.78, 37.86, 52.18, 59.97, 121.38 (m), 123.06 (m), 126.15, 127.10 (m), 128.51, 128.61, 134.96 (m), 142.24, 163.59; $^{19}$F NMR, δ 88.65 (p, J=150 Hz, 1F), 74.30 (d, J=150 Hz, 4F); HRMS, calcd. for C$_{18}$H$_{22}$F$_5$NO$_2$S, 411.1291; found, 411.1277; Anal. calcd for C$_{18}$H$_{22}$F$_5$NO$_2$S: C, 50.55; H, 5.39; N, 3.40; found: C, 52.73; H, 5.42; N, 3.28.

Methyl 1-tert-butyl-4-pentafluorosulfanyl-3-phenylpyrrole-2-carboxylate, compound 6b: (53%) mp 108-110° C.; $^1$H NMR, δ 1.66 (s, 9H), 3.34 (s, 3H), 7.18-7.31 (m, 6H); $^{13}$C NMR, δ 30.71, 52.00, 59.83, 121.67 (m), 122.70 (m), 126.93 (m), 127.39, 127.44, 130.12, 134.27, 135.20 (m), 163.93; $^{19}$F NMR, δ 87.35 (p, J=153 Hz, 1F), 75.40 (d, J=153 Hz, 4F); HRMS, calcd for C$_{16}$H$_{22}$F$_5$NO$_2$S, 383.0978; found, 383.0973; Anal. calcd for C$_{16}$H$_{18}$F$_5$NO$_2$S: C, 50.13; H, 4.73; N, 3.65; found: C, 50.42; H, 4.61; N, 3.36.

Methyl 1-tert-butyl-4-pentafluorosulfanyl-3-butylpyrrole-2-carboxylate, compound 6c: (54%) mp 41-44° C.; $^1$H NMR, δ 0.88-0.93 (t, J=14.4 Hz, 3H), 1.13-1.50 (m, 4H), 1.64 (s, 9H), 2.63-2.69 (t, J=15.9 Hz, 2H), 3.86 (s, 3H), 7.26 (s, 1H); $^{13}$C NMR, δ 13.97, 23.31, 25.94, 30.75, 33.77, 52.06, 59.71, 121.07 (m), 122.67 (m), 128.12 (m), 134.86 (m), 163.70; $^{19}$F NMR, δ 88.75 (p, J=155 Hz, 1F), 74.25 (d, J=155 Hz, 4F); HRMS, calcd. for C$_{14}$H$_{22}$F$_5$NO$_2$S, 363.1291; found, 363.1316; Anal, calcd for C$_{14}$H$_{22}$F$_5$NO$_2$S: C, 46.27; H, 6.10; N, 3.85; found: C, 46.39; 6.40; N, 3.93.

Methyl 1-tert-butyl-4-pentafluorosulfanyl-3-p-tolylpyrrole-2-carboxylate, compound 6d: (78%) mp 114-116° C., $^1$H NMR, δ 1.68 (s, 9H), 2.36 (s, 3H), 3.41 (s, 3H), 7.12 (s, 4H), 7.33 (s, 1H); $^{13}$C NMR, δ 21.42, 30.71, 52.05, 59.72, 121.52 (m), 122.72 (m), 126.76 (m), 128.15, 129.95, 131.11, 135.29 (m), 136,99, 164.08; $^{19}$F NMR, δ 87.63 (p, J=152 Hz, 1F), 75.44 (d, J=152 Hz, 4F); HRMS, calcd. for C$_{17}$H$_{20}$F$_5$NO$_2$S, 397.1135; found, 397.1120; Anal, calcd for C$_{17}$H$_{20}$F$_5$NO$_2$S: C, 51.38; H, 5.07; N, 3.52; found: C, 51.40; H, 5.25; N, 3.30.

To demonstrate the efficacy of the procedure, the tent-butyl group of pyrrole 6a was cleanly removed by treatment with catalytic quantities of triflic acid in methylene chloride to produce pyrrole 7 in a non-optimized yield of 72%.

Removal of tert-butyl Groups

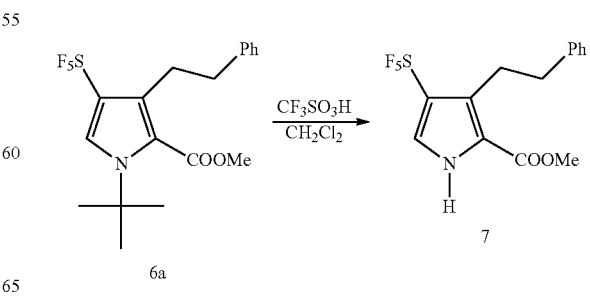

Procedure for Removal of tert-butyl Groups

Methyl 4-pentafluorosulfanyl-3-(2-phenylethyl)pyrrole-2-carboxylate, compound 7. Two drops of $CF_3SO_3H$ was added to a flask containing 80 mg 6a and 2 mL $CH_2Cl_2$ at RT, and the mixture was stirred for about 2 h (monitored by TLC). The mixture was purified directly by column chromatograph to obtain 7 as a white solid (78%): mp 165-167° C., $^1$H NMR, δ 2.78-2.84 (dd, J=8.1 & 4.2 Hz, 2H), 3.16-3.22 (dd, J=8.1 & 4.2 Hz, 2H), 3.92 (s, 3H), 7.19-7.34 (m, 6H), 9.34 (s, 1H); $^{13}$C NMR, δ 28.38, 37.49, 52.12, 118.81 (m), 122.02 (m), 126.19, 128.00 (m), 128.58, 128.61, 138.50 (m), 142.07, 161.26; $^{19}$F NMR, δ 88.87 (p, J=148 Hz, 1H), 73.56 (d, J=148 Hz, 4H); HRMS, calc for $C_{14}H_{14}F_5NO_2S$, 355.0665; found, 355.0648; Anal, calc for $C_{14}H_{14}F_5NO_2S$: C, 47.32; H, 3.97; N, 3.94; found: C, 47.04; H, 3.68; N, 3.86.

EXAMPLE 3

Pyrrolines and Pyrroles

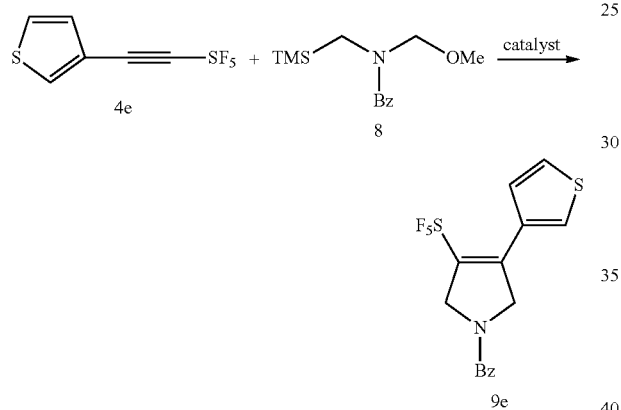

TABLE 1

Reaction Conditions

| entry | 8(equiv) | Catalyst[a] | solvent | T(° C.) | Conversion(%)[b] |
|---|---|---|---|---|---|
| 1 | 2 | CsF | $CH_3CN$ | rt | NR |
| 2 | 2 | CsF | $CH_3CN$ | reflux | NR |
| 3 | 2 | LiF | $CH_3CN$ | rt | NR |
| 4 | 2 | LiF | $CH_3CN$ | reflux | NR |
| 5 | 2 | TBAF | THF | rt | 100[c] |
| 6 | 2 | TFA | $CH_2Cl_2$ | rt | 65 |
| 7 | 4 | TFA | $CH_2Cl_2$ | rt | 100 |
| 8 | 2.5 | TFA | $CH_2Cl_2$ | reflux | 100[d] |

[a] 2equiv of fluorine catalyst or 0.2equiv TFA was used;
[b] after 24 hs;
[c] no desired product obtained;
[d] 96% isolated yield.

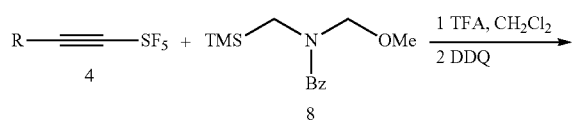

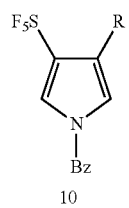

TABLE 2

| entry | substrate | Yield(%) |
|---|---|---|
| 1 | 4a | 79 |
| 2 | 4b | 80 |
| 3 | 4d | 88 |
| 4 | 4e | 96 |
| 5 | 4f | 78 |

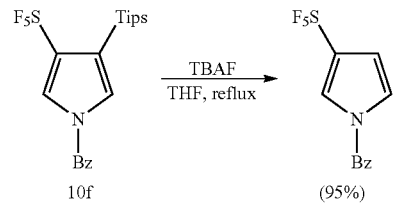

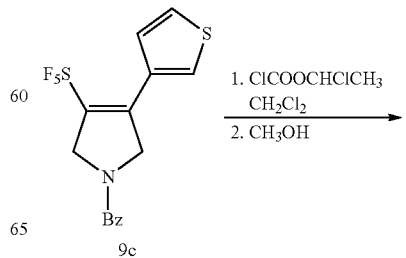

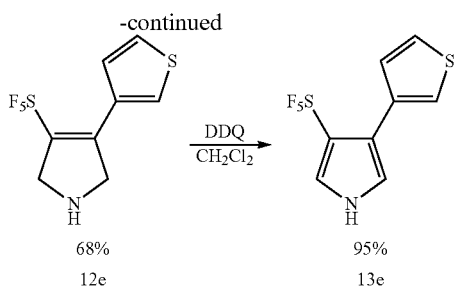

68% 12e → 95% 13e

Experimental Section

NMR spectras were obtained in $CDCl_3$ using TMS and $CFCl_3$ as the internal standards for $^1H/^{13}C$ NMR and $^{19}F$ NMR respectively, melting points were uncorrected. Starting materials SF5-alkyne compounds 1a-e were prepared according to the previous literature.

1-pentafluorosulfanyl-2-(3-thienyl)-acetylene(4e):(60%) $^1$HNMR ($CDCl_3$), δ7.18-7.20 (dd, J=1.2, 3.6 Hz, 1H), 7.32-7.34 (dd, J=3.0, 2.1 Hz, 1H), 7.73-7.34 (m, 1H); $^{13}$CNMR, δ126.7, 129.8 (m), 134.0 (m); $^{19}$FNMR, δ83.6 (m, 4F), 76.9 (m, 1F).

General procedure for preparation of pyrroles 10a-f. Trifluoroacetic acid (TFA) solution (0.9 ml, 0.2 equiv, 1M in $CH_2Cl_2$) was slowly added to a mixture of 4 (4.27 mmol, 1 equiv) and N-(methoxymethyl)-N-(trimethylsilylmethyl)-benzylamine 8 (10 mmol, 2.5 equiv) in 10 ml $CH_2Cl_2$. After addition, the reaction mixture was refluxed for 24 hs, and then cooled with an ice-water bath. DDQ (4.7 mmol, 1.1 equiv) was carefully added to the light-yellow solution. With stirred for another 2 hs, the dark-red mixture was diluted with 10 ml $CH_2Cl_2$ and poured into saturated $NaHCO_3$ solution (20 ml), separated the organic phase and evaporated the solvent. The residue was submitted to column chromatography. The products were obtained as white solids or colorless liquids.

The intermediate 9e was separated and characterized by NMR analysis prior to its oxidative conversion to pyrrole 10e.

1-benzyl-3-pentafluorosulfanyl-4-(3-thienyl)-2,5-dihydro-pyrrole(9e): $^1$HNMR (CD$Cl_3$), δ3.79 (s, 2H), 3.84-3.87 (m, 2H), 4.00-4.03 (t, J=4.2 Hz, 2H), 7.13-7.14 (d, J=4.8 Hz, 1H), 7.26-7.36 (m, 7H); $^{13}$CNMR, δ60.1, 61.8 (m), 64.8, 125.5 (m), 125.7, 127.6 (m), 127.7, 128.8, 128.9, 132.5, 137.0 (m), 138.1, 144.4 (m); $^{19}$FNMR, δ83.9 (p, J=164 Hz, 1F), 66.4 (d, J=166 Hz, 4F).

1-benzyl-3-pentafluorosulfanyl-4-(3-thienyl)-pyrrole (10e):(96%) mp 69-71° C. $^1$HNMR ($CDCl_3$), δ5.00 (s, 2H), 6.57 (s, 1H), 7.13-7.15 (m, 2H), 7.19-7.23 (m, 3H), 7.25-7.28 (m, 1H), 7.35-7.42 (m, 3H); $^{13}$CNMR, δ54.3, 117.5 (m), 120.3 (m), 122.1 (m), 123.1, 124.6, 127.9, 128.7, 129.30, 129.5 (m), 134.3, 135.9; $^{19}$FNMR, δ88.4 (p, J=168 Hz, 1F), 75.7 (d, J=163 Hz, 4F). HRMS: calcd for $C_{15}H_{12}F_5NS_2$, 365.0331; found, 365.0319. Anal. Calcd for $C_{15}H_{12}F_5NS_2$: C, 49.31; H, 3.31; N, 3.76. Found: C, 49.58; H, 3.25; N, 3.76.

1-benzyl-3-pentafluorosulfanyl-4-(2-phenylethyl)-pyrrole(10a):(79%) $^1$HNMR ($CDCl_3$), δ2.93 (m, 4H), 4.95 (s, 2H), 6.33 (s, 1H), 7.06-7.07 (d, J=2.4 Hz, 1H), 7.13-7.16 (m, 2H), 7.22-7.25 (m, 3H), 7.30-7.37 (m, 2H), 7.38-7.44 (m, 3H); $^{13}$CNMR, 828.6, 36.8, 54.1, 118.9 (m), 120.7 (m), 121.6 (m), 126.2, 127.6, 128.50, 128.6, 128.7, 129.2, 136.4, 142.0; $^{19}$FNMR, δ89.6 (p, J=164Hz, 1F), 74.6 (d, J=161 Hz, 4F). HRMS: calcd for $C_{17}H_{18}F_5NS$, 387.1080; found, 388.1153 (M+H). Anal. Calcd for $C_{17}H_{18}F_5NS$: C, 58.90; H, 4.68; N, 3.62. Found: C, 58.74; H, 4.29; N, 3.78.

1-benzyl-3-pentafluorosulfanyl-4-phenyl-pyrrole(10b): (80%) $^1$HNMR ($CDCl_3$), δ5.05 (s, 2H), 6.56 (s, 1H), 7.19 (s, 1H), 7.26-7.28 (d, J=7.5 Hz, 2H), 7.37-7.44 (m, 8H); $^{13}$CNMR, δ54.3, 120.3, 121.8, 122.9, 127.3, 127.8, 127.9, 128.7, 129.3, 130.1, 134.9, 135.9; $^{19}$FNMR, δ88.6 (p, J=169 Hz, 1F), 76.2 (d, J=163 Hz, 4F). HRMS: calcd for $C_{17}H_{14}F_5NS$, 359.0767; found, 359.0786. Anal. Calcd for $C_{17}H_{14}F_5NS$: C, 56.82; H, 3.93; N, 3.90. Found: C, 56.47; FI, 3.82; N, 4.01.

1-benzyl-3-pentafluorosulfanyl-4-tolyl-pyrrole(10d): (88%) $^1$HNMR ($CDCl_3$), δ2.43 (s, 3H), 5.05 (s, 2H), 6.54 (s, 1H), 7.18-7.23 (m, 3H), 7.25-7.28 (m, 2H), 7.32-7.35 (m, 2H), 7.40-7.45 (m, 3H); $^{13}$CNMR, δ21.4, 54.2, 120.1, 121.6, 122.8, 127.8, 128.6, 129.2, 129.9, 131.9, 135.9, 136.9; $^{19}$FNMR, δ88.6 (p, J=160 Hz, 1F), 76.1 (d, J=150 Hz, 4F). FIRMS: calcd for $C_{18}H_{16}F_5NS$, 373.0923; found, 373.0921. Anal. Calcd for $C_{18}H_{16}F_5NS$: C, 57.90; H, 4.32; N, 3.75. Found: C, 57.65; H, 4.35; N, 3.80.

1-benzyl-3-pentafluorosulfanyl-4-triisopropylsilyl-pyrrole(10f): (78%) mp 37-39° C. $^1$HNMR ($CDCl_3$), δ1.07-1.09 (d, J=7.2 Hz, 18H), 1.31-1.41 (m, 3H), 5.05 (s, 2H), 6.67 (s, 1H), 7.08-7.11 (m, 2H), 7.18-7.19 (m, 1H), 7.31-7.39 (m, 3H); $^{13}$CNMR, 612.6, 19.3, 53.8, 110.9 (m), 123.6 (m), 127.2, 128.4, 129.2, 129.4, 136.5, 142.5 (m); $^{19}$FNMR, δ89.4 (p, J=164 Hz, 1F), 72.6 (d, J=156 Hz, 4F). HRMS: calcd for $C_{20}H_{30}F_5NSSi$, 439.1788; found, 440.1859 (M+H). Anal. Calcd for $C_{20}H_{30}F_5NSSi$: C, 54.64; H, 6.88; N, 3.19. Found: C, 54.67; H, 6.62; N, 3.19.

1-benzyl-3-pentafluorosulfanyl-pyrrole(11): 0.9 ml TBAF (1M in TI-IF) was added to a round flask containing 10f (200 mg, 0.455 mmol) and 3 ml THF, then it was heated to reflux overnight. The mixture was poured into water (5 ml), extracted with $CH_2Cl_2$(5 ml×3), removed the solvent and the residue was submitted to column. 0.12 g product was obtained as colorless oil (95%). $^1$HNMR ($CDCl_3$), δ5.04 (s, 2H), 6.43-6.45 (m, 1H), 6.60 (s, 1H), 7.05 (s, 1H), 7.15-7.18 (m, 2H), 7.32-7.42 (m, 3H); $^{13}$CNMR, δ54.2, 107.3 (m), 120.1 (m), 120.4, 127.6, 128.6, 129.2, 136.2; $^{19}$FNMR, δ87.6 (p, J=162 Hz, 1F), 70.8 (d, J=163 Hz, 4F). HRMS: calcd for $C_{11}H_{10}F_5NS$, 283.0454; found, 283.0458. Anal. Calcd for $C_{11}H_{10}F_5NS$: C, 46.64; H, 3.56; N, 4.94. Found: C, 46.82; H, 3.55; N, 5.15.

1-hydro-3-pentafluorosulfanyl-4-(3-thienyl)-2,5-dihydropyrrole(12e): 1-chloroethyl chloroformate (156 mg, 1.1 mmol) was added to a solution of 3a (200 mg, 0.55 mmol) and triethylamine (55 mg, 0.55 mmol) in 2 ml $CH_2Cl_2$ at 0° C. with stirring, the mixture was then concentrated after 30 mins, dissolved in methanol (2 ml) and stirred overnight. Removed the solvent and the residue was submitted to column. 102 mg colorless oil was obtained (68%). $^1$HNMR ($CDCl_3$), δ2.17 (s, 2H), 4.06 (m, 2H), 4.19-4.21 (t, J=7.2 Hz, 2H), 7.10-7.11 (d, J=4.8 Hz, 1H), 7.26-7.29 (m, 1H), 7.33-7.34 (m. 1H); $^{13}$CNMR, δ56.9 (m), 59.8, 125.2 (m), 125.7, 127.5, 132.2, 139.1 (m), 147.1 (m); $^{19}$FNMR, δ84.2 (p, J=162 Hz, 1F), 67.4 (d, J=164 Hz, 4F).

1-hydro-3-pentafluorosulfanyl-4-(3-thienyl)-pyrrole (13e): DDQ (125 mg, 0.66 mmol) was added to a solution of 5 in $CH_2Cl_2$ at 0° C. with stirring, after standing for 2 hs, the mixture was submitted to column directly. 95 mg colorless oil was obtained (95%). $^1$HNMR ($CDCl_3$), δ6.67 (s, 1H), 7.12-7.14 (d, J=5.1 Hz, 1H), 7.21-7.22 (m, 2H), 7.26-7.29 (m, 1H), 8.43 (s, 1H); $^{13}$CNMR, δ117.4 (m), 119.4 (m), 123.2, 124.7, 129.6, 134.1, 136.6 (m); $^{19}$FNMR, δ87.9 (p, J=167 Hz, 1F), 75.5 (d, J=163 Hz, 4F). HRMS: calcd for $C_8H_6F_5NS_2$, 274.9862; found, 274.9864. Anal. Calcd for $C_8H_6F_5NS_2$: C, 34.91; H, 2.20; N, 5.09. Found: C, 35.29; H, 2.25; N, 4.75.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein are incorporated by reference in their entirety, including all figures and tables, to the extent they are not inconsistent with the explicit teachings of this specification.

We claim:

1. An $F_5S$ substituted heterocycle of:

compound (A):

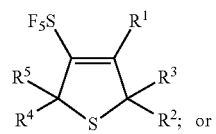

compound (B):

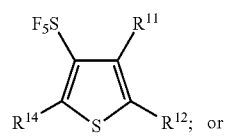

compound (C):

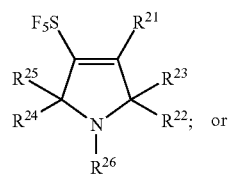

compound (D):

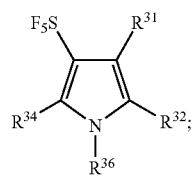

wherein $R^1$, $R^2$, $R^3$, $R^4$, $R^5$, $R^{11}$, $R^{12}$, $R^{14}$, $R^{21}$, $R^{22}$, $R^{23}$, $R^{24}$, $R^{25}$, $R^{26}$, $R^{31}$, $R^{32}$, $R^{34}$, and $R^{36}$ are independently selected from hydrogen, halo, hydroxy, azido, cyanoato, isocyano, isocyanato, nitroxy, cyano, nitrosooxy, nitro, nitroso, thiocyanato, substituted or unsubstituted alkyl, substituted or unsubstituted alkenyl, substituted, or unsubstituted alkynyl, substituted or unsubstituted aryl, substituted or unsubstituted, heteroaryl, substituted or unsubstituted heterocyclic, substituted or unsubstituted alkoxy, substituted or unsubstituted aryloxy, substituted or unsubstituted carbonyl, substituted or unsubstituted carboxyl, substituted or unsubstituted carbonate, substituted or unsubstituted silyl, substituted or unsubstituted siloxy, substituted or unsubstituted peroxy, substituted or unsubstituted amino, substituted or unsubstituted imido, substituted or unsubstituted phospho, substituted or unsubstituted phosphine, substituted or unsubstituted phosphono, substituted or unsubstituted sulfanyl, substituted or unsubstituted carbonylsulfinyl, substituted or unsubstituted sulfonyl, and substituted or unsubstituted sulfinyl.

2. The $F_5S$ substituted heterocycle of claim 1, wherein $R^1$, $R^{11}$, $R^{21}$, or $R^{31}$ is substituted or unsubstituted alkyl, substituted or unsubstituted aryl, substituted or unsubstituted heteroaryl, or substituted or unsubstituted silyl.

3. The $F_5S$ substituted heterocycle of claim 1, wherein $R^1$, $R^{11}$, $R^{21}$, or $R^{31}$ is p-tolyl, 2-phenylethyl, phenyl, thienyl, butyl tri-i-propylsilyl or hydrogen.

4. The $F_5S$ substituted heterocycle of claim 1, wherein $R^2$, $R^3$, $R^4$, and $R^5$ are hydrogen.

5. The $F_5S$ substituted heterocycle of claim 1, wherein $R^{12}$ and $R^{14}$ are hydrogen.

6. The $F_5S$ substituted heterocycle of claim 1, wherein $R^{23}$, $R^{24}$, and $R^{25}$ are hydrogen and $R^{22}$ is $C(=O)OMe$ or hydrogen.

7. The $F_5S$ substituted heterocycle of claim 1, wherein $R^{34}$ is hydrogen and $R^{32}$ is $C(=O)OMe$ or hydrogen.

8. The $F_5S$ substituted heterocycle of claim 1, wherein $R^{26}$ is hydrogen, t-butyl, or benzyl.

9. The $F_5S$ substituted heterocycle of claim 1, wherein $R^{36}$ is hydrogen, t-butyl, or benzyl.

10. A method of synthesizing an SF5-substituted heterocycle according to claim 1, comprising:
providing an $SF_5$-substituted alkyne;
contacting said alkyne with an 1,3-dipolar species having an N or S atom in the species or its synthetic precursor or synthetic equivalent to form a non-aromatic SF5-substituted heterocycle of compound (A) or compound (C); and
optionally, oxidizing the non-aromatic SF5-substituted heterocycle of compound (A) to aromatic SF5-substituted heterocycle of compound (B) or the non-aromatic SF5-substituted heterocycle of compound (C) to aromatic SF5-substituted heterocycle of compound (D).

11. The method of claim 10, wherein the 1,3-dipolar species is a thiocarbonyl ylide its synthetic precursor, or synthetic equivalent to form the non-aromatic SF5-substituted heterocycle of compound (A).

12. The method of claim 10, wherein the 1,3-dipolar species is an azomethine ylide, its synthetic precursor, or synthetic equivalent to form the non-aromatic SF5-substituted heterocycle of compound (C).

13. The method of claim 10, further comprising converting a nitrogen protecting substituent $R^{26}$ of the non-aromatic SF5-substituted heterocycle of compound (C) or a nitrogen protecting substituent $R^{36}$ of the aromatic SF5-substituted heterocycle of compound (D) to a hydrogen.

14. The method of claim 13, wherein the protecting substituent is t-buty or benzyl.

15. The method of claim 10, further comprising converting a trialkylsilyl substituent to a hydrogen.

16. The method of claim 15, wherein the trialkylsilyl substituent is at $R^1$, $R^{11}$, $R^{21}$, or $R^{31}$.

17. The method of claim 15, wherein the trialkylsilyl substituent is tri-i-propylsilyl.

* * * * *

UNITED STATES PATENT AND TRADEMARK OFFICE
CERTIFICATE OF CORRECTION

Figure 5A:
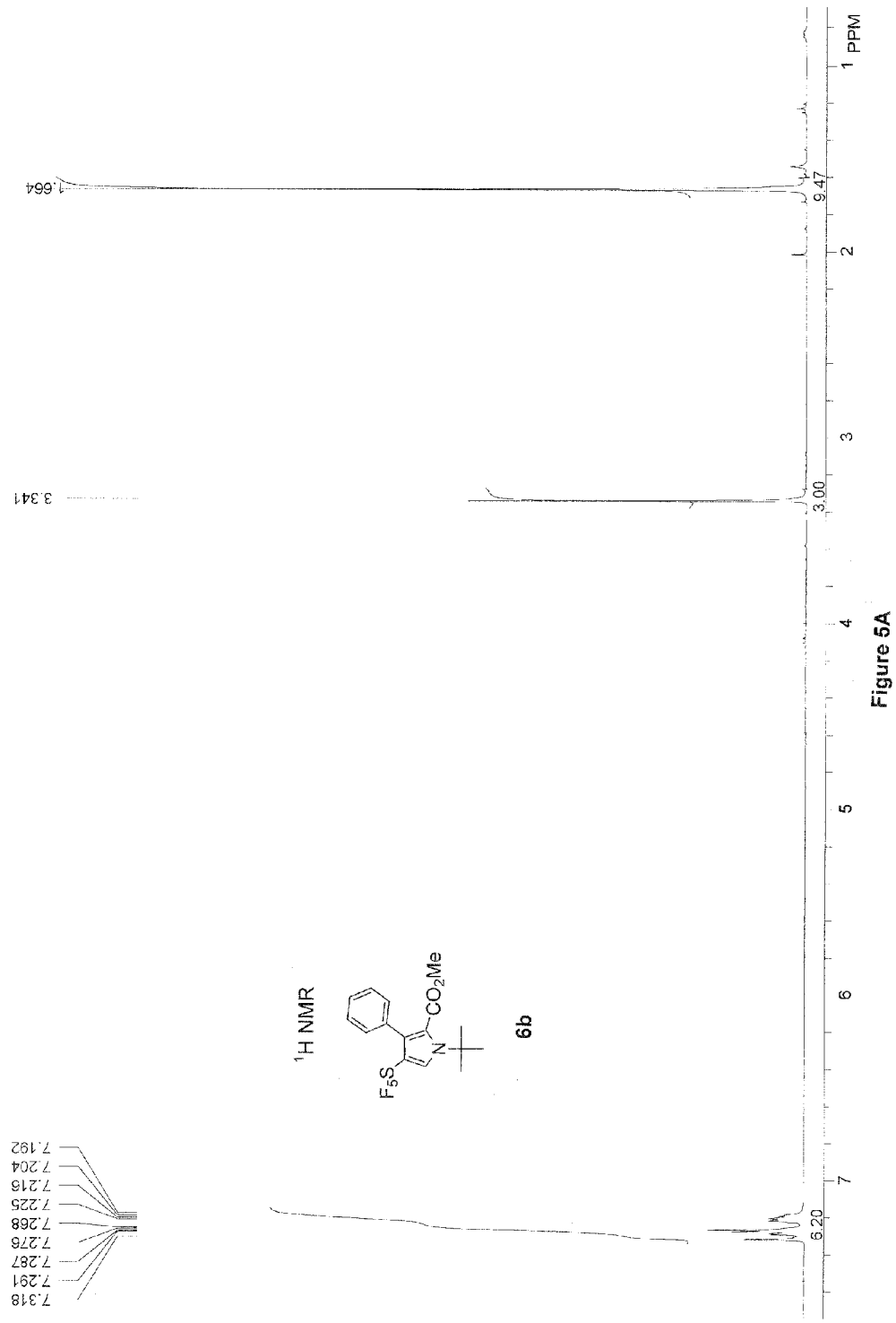
FIGS. 5A-5C present NMR spectra for compound 6b.
Figure 5B:
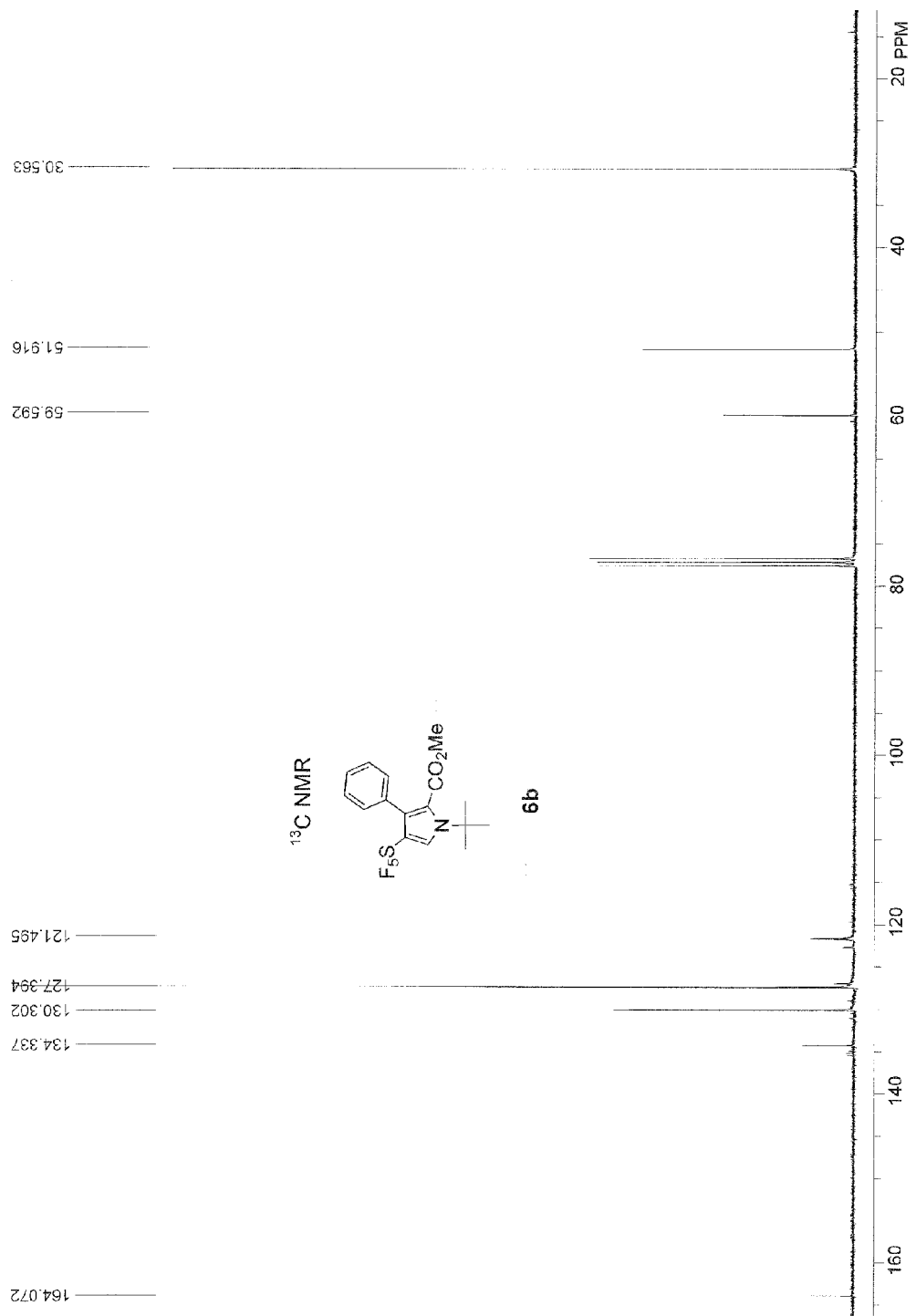
Figure 5C:
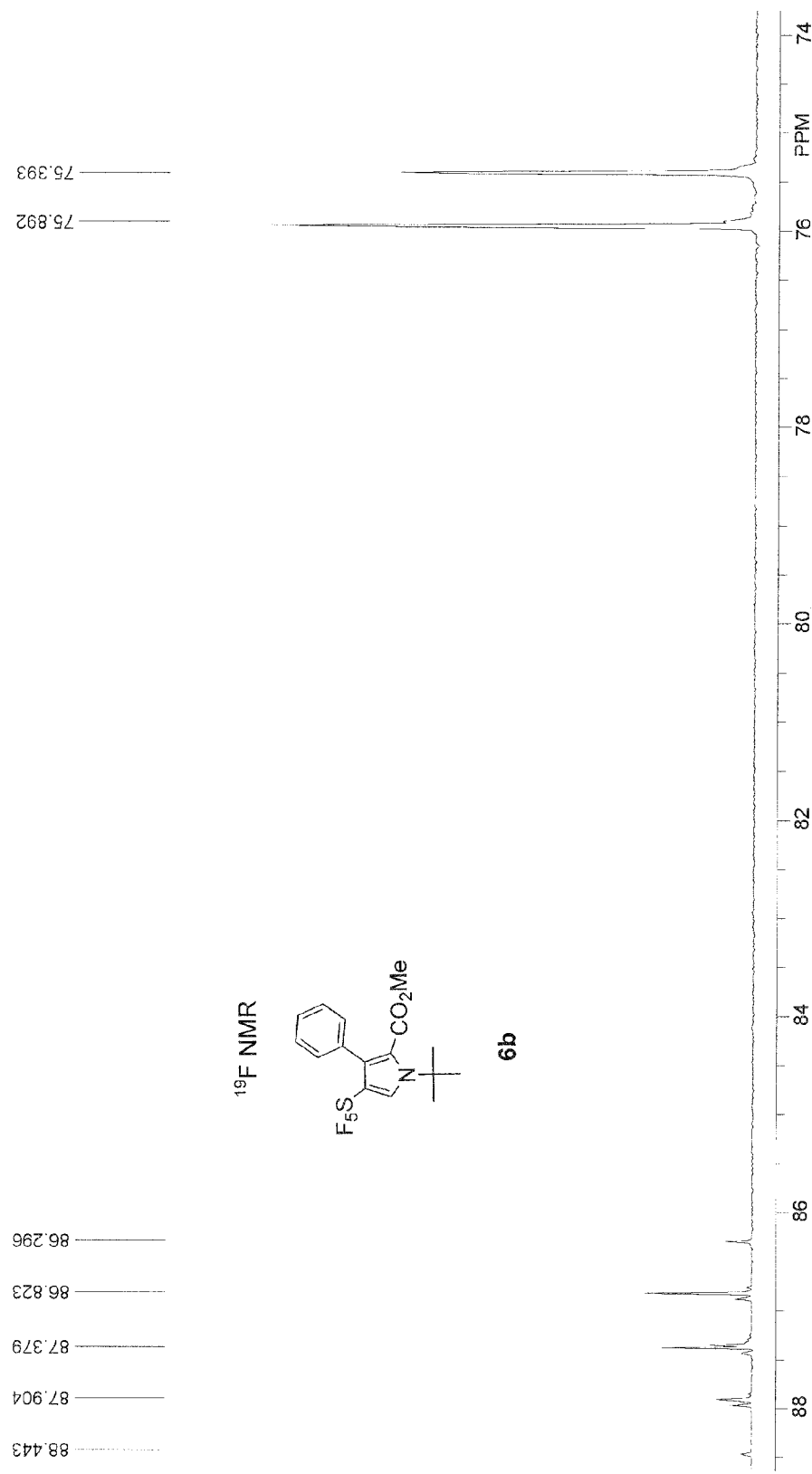
Figure 6A:
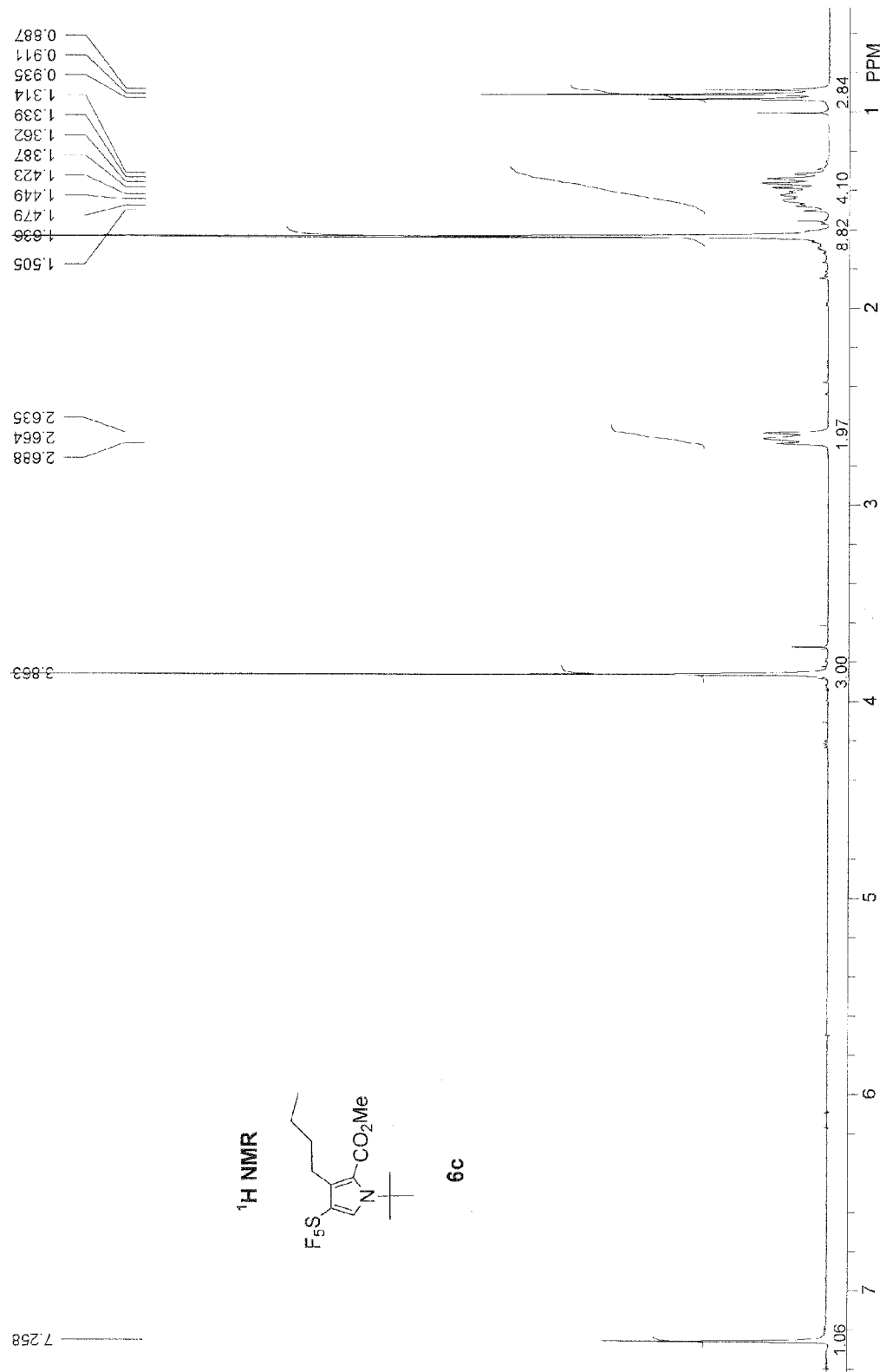
FIGS. 6A-6C present NMR spectra for compound 6c.
Figure 6B:
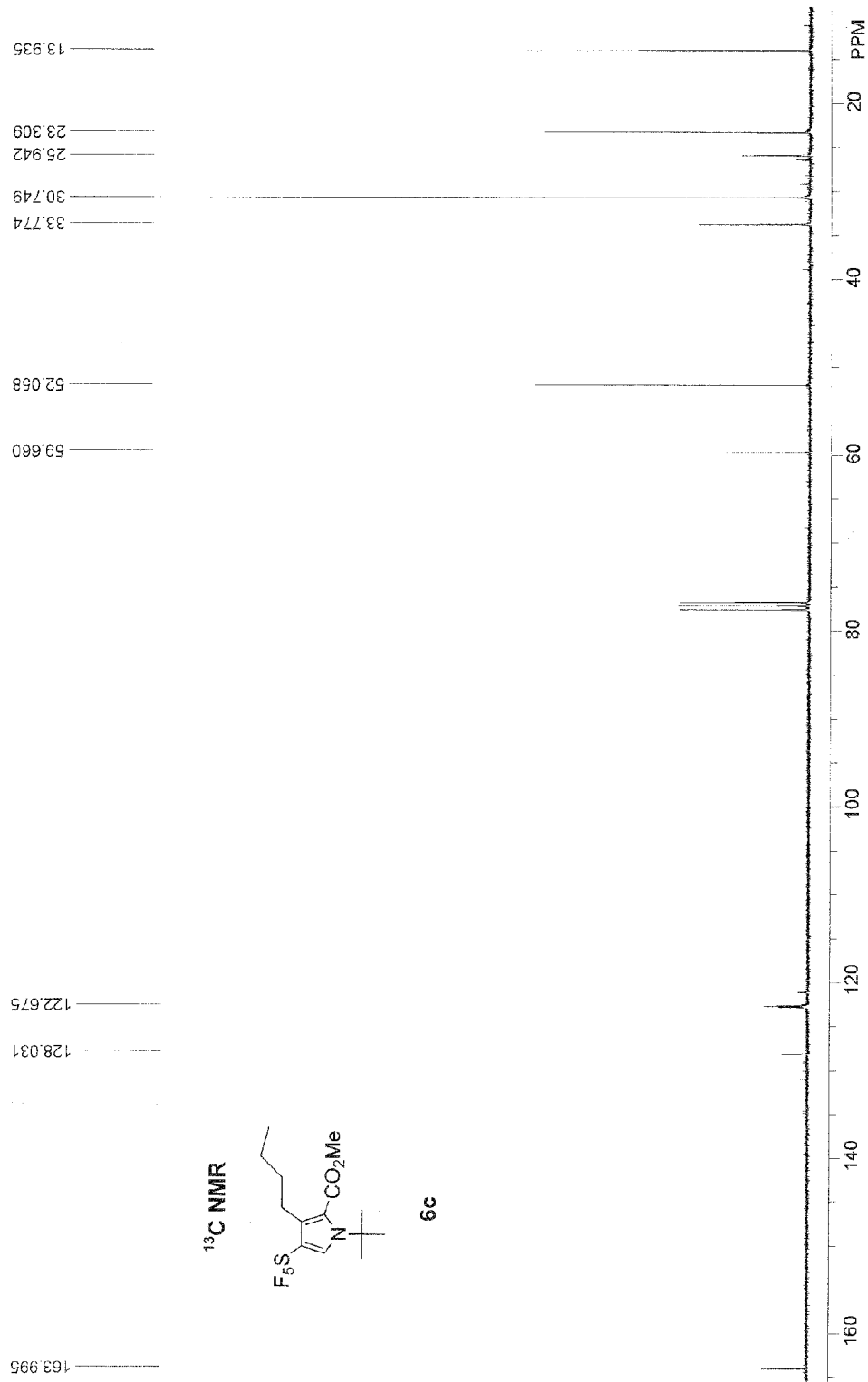
Figure 6C:
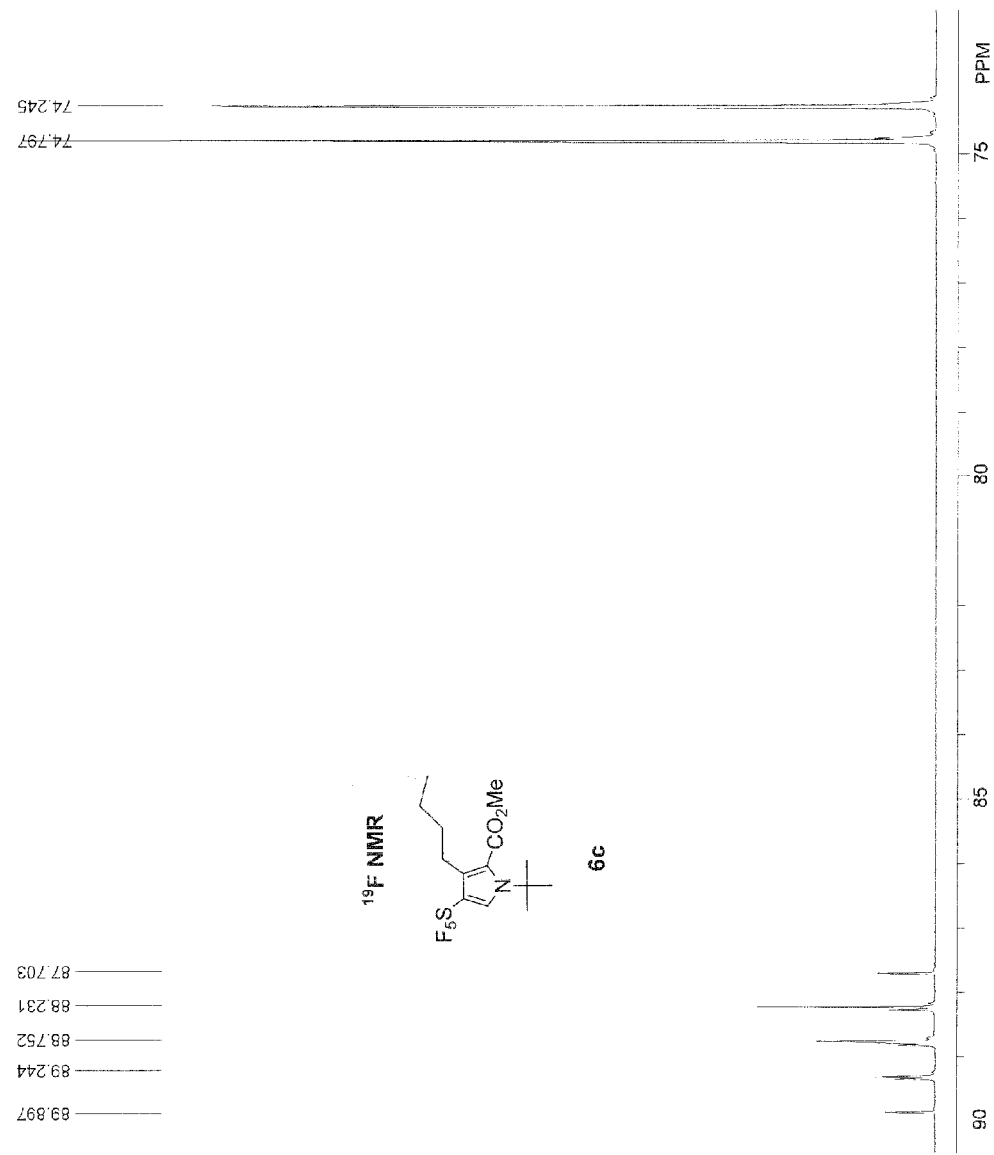
Figure 7A:
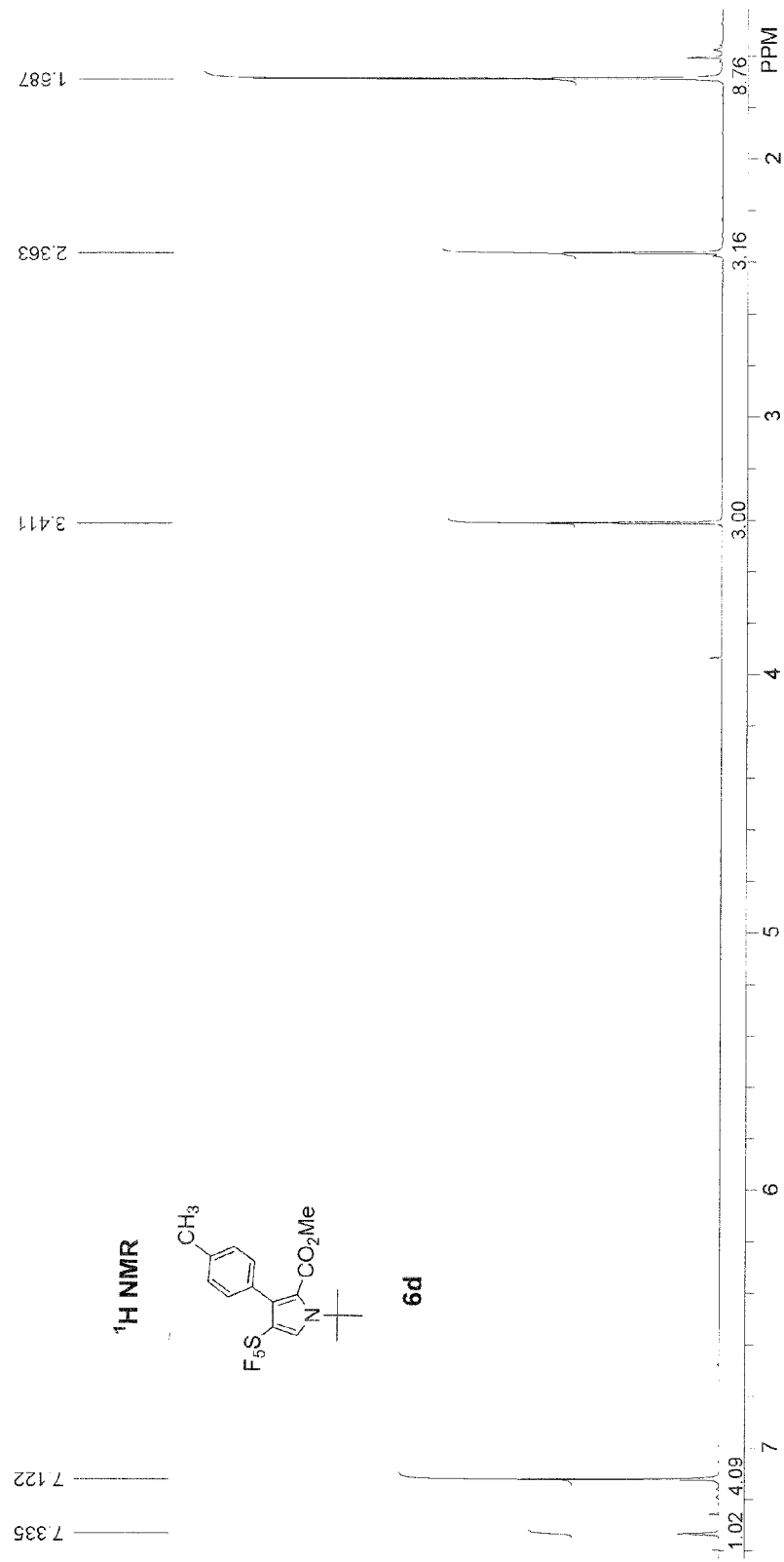
Figure 7C:
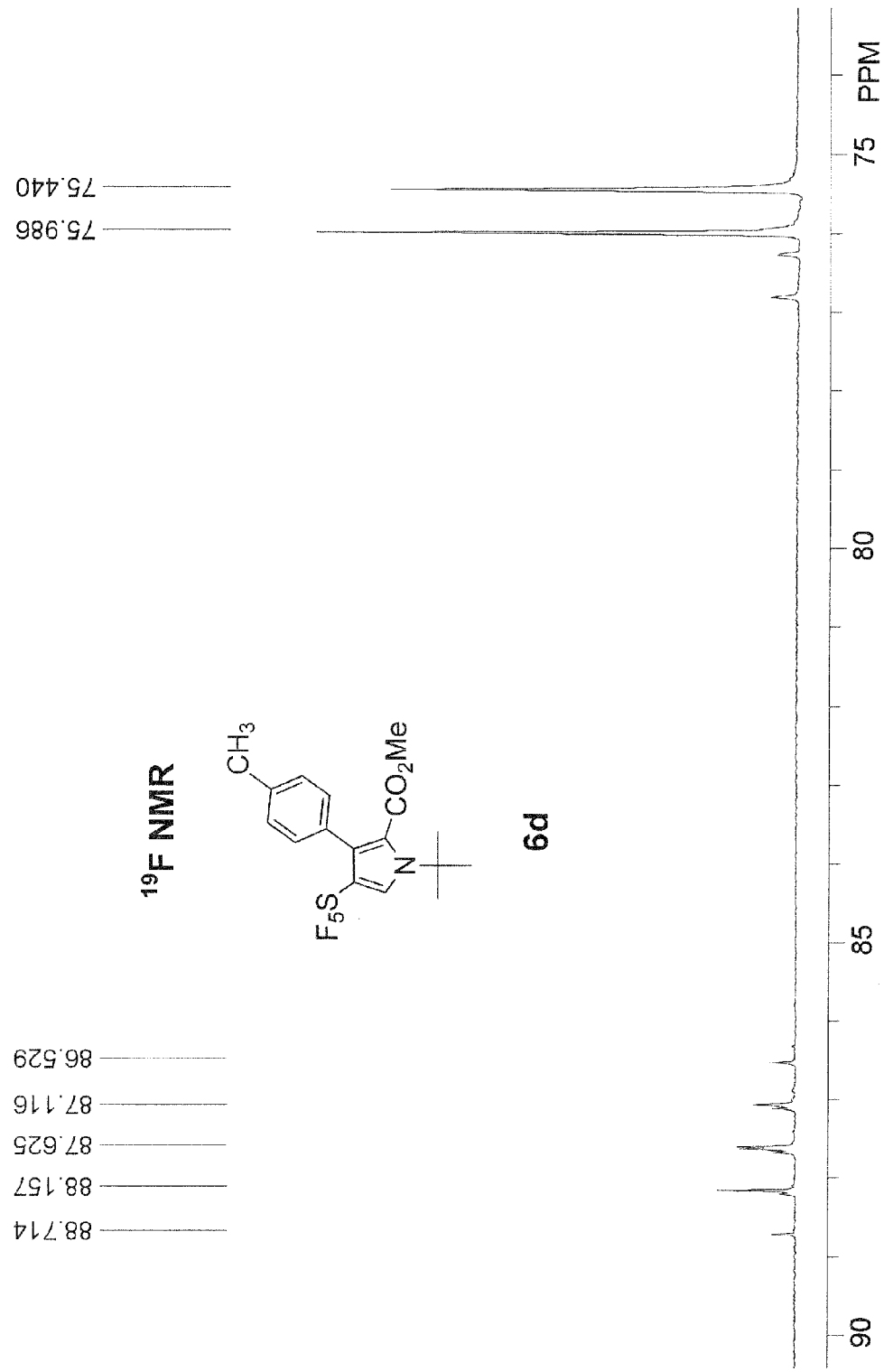
Figure 8A:
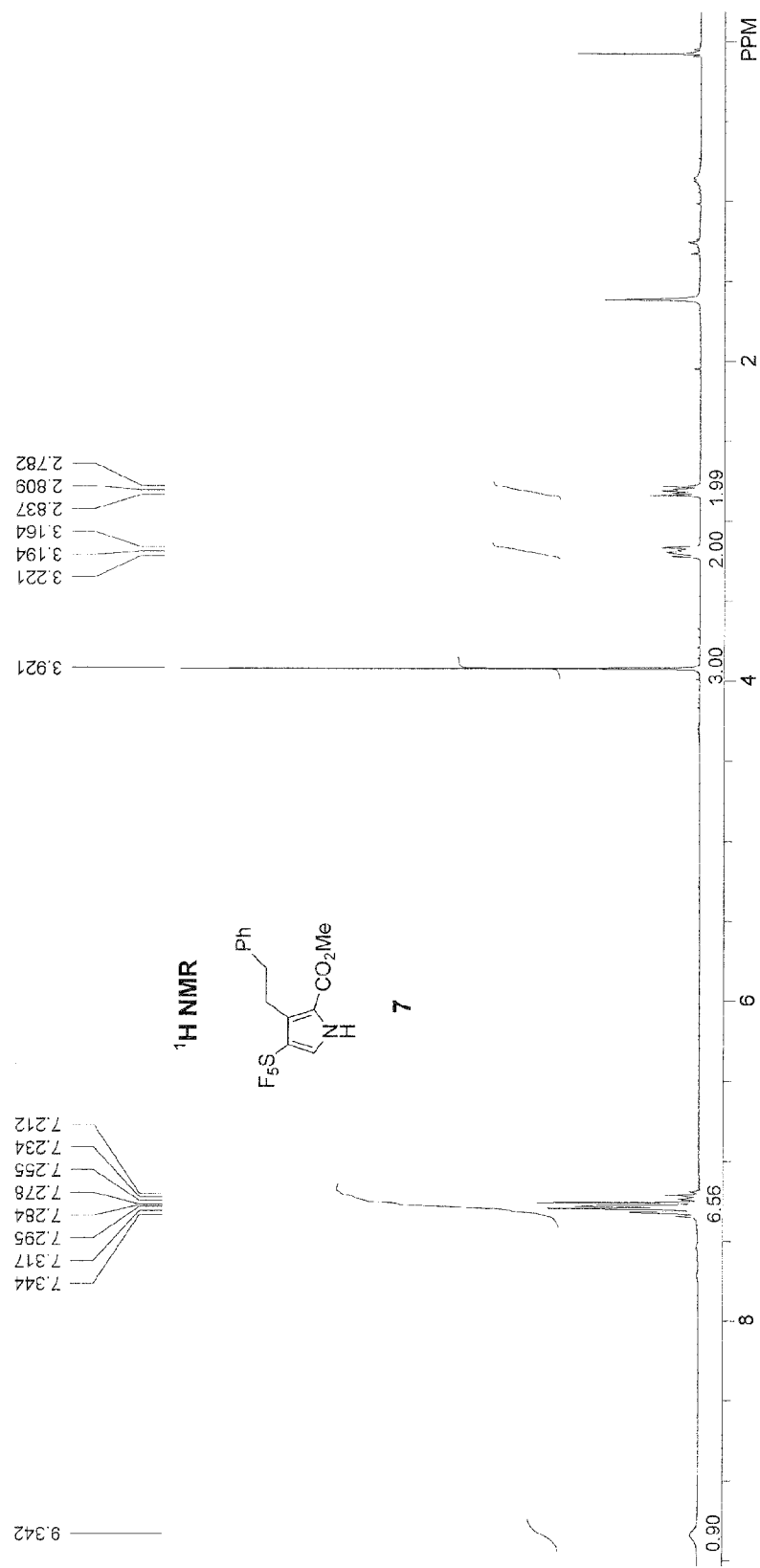
FIGS. 8A-8C present NMR spectra for compound 7.
Figure 8B:
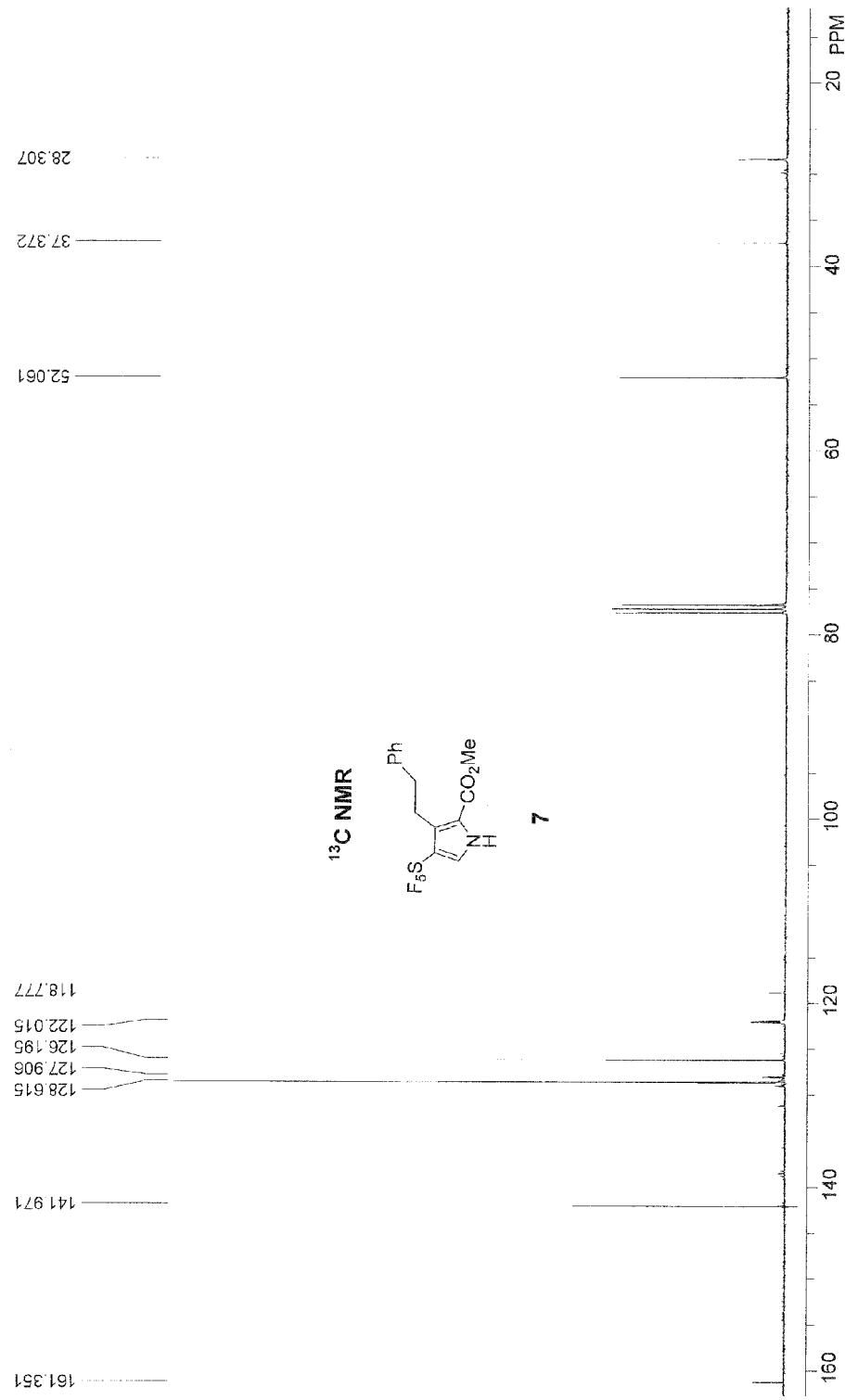
Figure 8C:
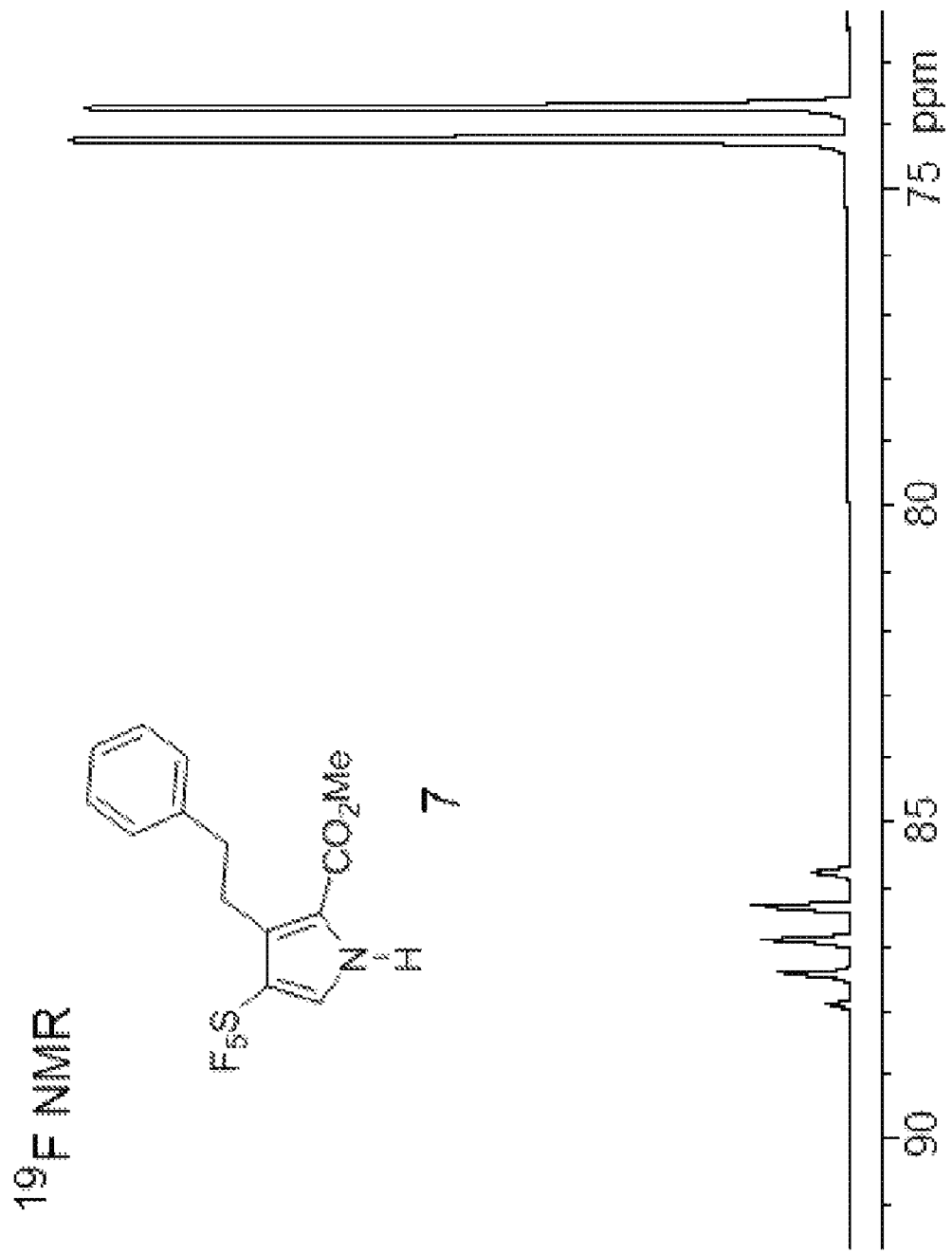

PATENT NO. : 7,943,787 B2
APPLICATION NO. : 12/817652
DATED : May 17, 2011
INVENTOR(S) : Zhaoyun Zheng and William R. Dolbier It is certified that error appears in the above-identified patent and that said Letters Patent is hereby corrected as shown below:

Column 2,
Lines 17-18, "compound 7. FIG. 5A is the" should read --compound 7. Figure 8A is the--.

Column 4,
Lines 28-29, "hydrogen or carbon.
    Carbonate, as used"
    should read --hydrogen or carbon. Carbonate, as used--.

Column 5,
Line 48, "tent-butyl" should read --tert-butyl--.
Line 55, "tent-butyl" should read --tert-butyl--.

Column 8,
Lines 35-40,

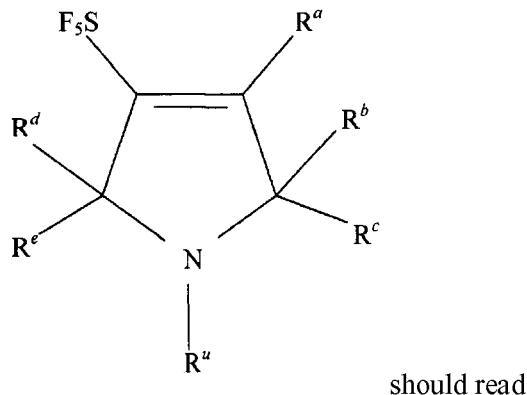

should read

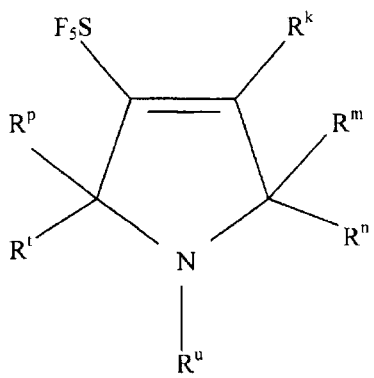

.

Column 8,
Line 67 through Column 9 line 1, "described above.
    Alternatively"
    should read --described above. Alternatively--.

Signed and Sealed this
Sixteenth Day of August, 2011

David J. Kappos
*Director of the United States Patent and Trademark Office*

CERTIFICATE OF CORRECTION (continued)
U.S. Pat. No. 7,943,787 B2

Column 13,
Lines 19-22,
"6a, CH₂CH₂Ph (60%);        should read        --6a, CH₂CH₂Ph (60%)
 6b, Ph (53%)                                    6b, Ph (53%)
 6c, n-Butyl (54%;                                6c, n-Butyl (54%)
 6d, p-tolyl (78%)"                               6d, p-tolyl (78%)--.
Line 51, "tent-butyl" should read --tert-butyl--.

Column 14,
Line 27, "$C_{16}H_{22}F_5NO_2S$" should read --$C_{16}H_{18}F_5NO_2S$--.
Line 39, "C, 46.39; 6.40; N, 3.93" should read --C, 46.39; H, 6.40; N, 3.93--.
Line 45, "(m), 136,99, 164.08" should read --(m), 136.99, 164.08--.
Line 49, "tent-butyl" should read --tert-butyl--.

Column 16,
Lines 57-66,

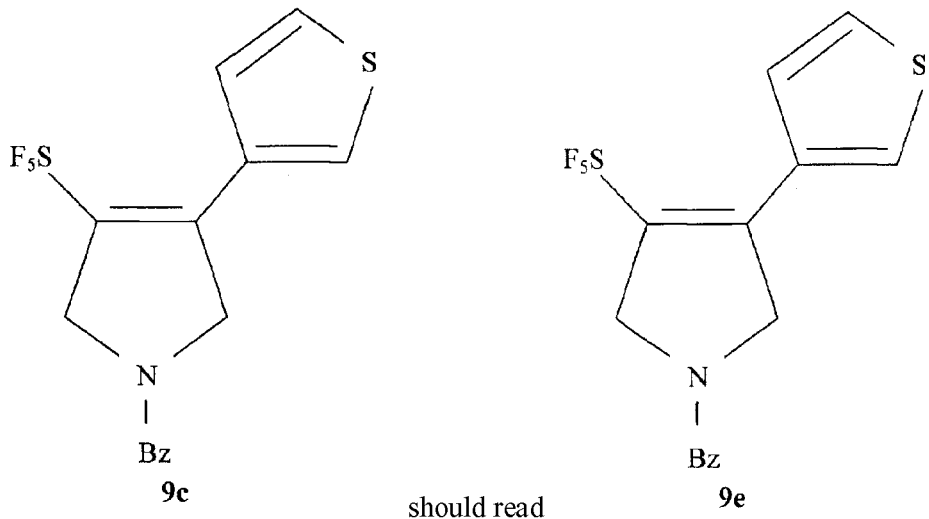

should read

Column 17,
Lines 32-33, "With stirred for" should read --While stirred for--.
Lines 60, "$^{13}$CNMR, δ28.6, 36.8," should read --$^{13}$CNMR, δ28.6, 36.8--.

Column 18,
Lines 6-7, "II, 3.93; N, 3.90. Found: C, 56.47; FI, 3.82;"
    should read --H, 3.93; N, 3.93. Found: C, 56.47; H, 3.82;--.
Line 14, "FIRMS:" should read --HRMS:--.
Line 18, "1-benzyl-3-pentafluorosulfanyl-4-triisopropylsilyl-pyr- role(100: (78%)"
    should read --1-benzyl-3-pentafluorosulfanyl-4-triisopropylsilyl-pyr- role(10f):(78%)--.
Line 21, "$^{13}$CNMR, δ12.5, 19.3" should read --$^{13}$CNMR, δ12.5, 19.3--.
Line 28, "(1M in TI-IF)" should read --(1M in THF)--.